United States Patent
Hollis et al.

(10) Patent No.: US 10,945,725 B2
(45) Date of Patent: Mar. 16, 2021

(54) IMPLANT INSERTER

(71) Applicant: CROSSROADS EXTREMITY SYSTEMS, LLC, Memphis, TN (US)

(72) Inventors: Michael Chad Hollis, Collierville, TN (US); Daniel Sayger, Southaven, MS (US)

(73) Assignee: CROSSROADS EXTREMITY SYSTEMS, LLC, Memphis, TN (US)

( * ) Notice: Subject to any disclaimer, the term of this patent is extended or adjusted under 35 U.S.C. 154(b) by 321 days.

(21) Appl. No.: 16/031,980

(22) Filed: Jul. 10, 2018

(65) Prior Publication Data

US 2018/0317906 A1   Nov. 8, 2018

Related U.S. Application Data

(63) Continuation-in-part of application No. PCT/US2018/016994, filed on Feb. 6, 2018.

(60) Provisional application No. 62/455,361, filed on Feb. 6, 2017.

(51) Int. Cl.
| | |
|---|---|
| *A61B 17/064* | (2006.01) |
| *A61B 17/068* | (2006.01) |
| *A61B 17/10* | (2006.01) |
| *A61F 2/46* | (2006.01) |

(52) U.S. Cl.
CPC ........ *A61B 17/0642* (2013.01); *A61B 17/068* (2013.01); *A61B 17/0644* (2013.01); *A61B 17/0682* (2013.01); *A61B 17/10* (2013.01); *A61B 2017/0645* (2013.01); *A61B 2017/0648* (2013.01); *A61F 2/4603* (2013.01); *A61F 2220/0025* (2013.01)

(58) Field of Classification Search
CPC ............ A61B 2017/0645; A61B 17/0682
See application file for complete search history.

(56) References Cited

U.S. PATENT DOCUMENTS

| | | |
|---|---|---|
| 2,010,913 A | 8/1935 | Bruce |
| 2,133,859 A | 10/1938 | Hawley |
| 2,544,492 A | 3/1951 | Downing |
| 2,811,073 A | 10/1957 | Klopstock |
| 3,741,205 A | 6/1973 | Markolf |
| 4,263,903 A | 4/1981 | Griggs |
| 4,278,091 A | 7/1981 | Borzone |
| 4,415,111 A | 11/1983 | McHarrie |
| 4,438,769 A | 3/1984 | Pratt |
| 4,454,875 A | 6/1984 | Pratt |
| 4,484,570 A | 11/1984 | Sutter |
| 4,655,222 A | 4/1987 | Florez |
| 4,723,540 A | 2/1988 | Gilmer, Jr. |
| 4,805,617 A | 2/1989 | Bedi |
| 4,848,328 A | 7/1989 | Laboureau |
| 4,852,558 A | 8/1989 | Outerbridge |

(Continued)

FOREIGN PATENT DOCUMENTS

| | | |
|---|---|---|
| CA | 2063484 | 9/1993 |
| CN | 2404495 | 11/2000 |

(Continued)

*Primary Examiner* — David W Bates
(74) *Attorney, Agent, or Firm* — Maywood IP Law; David Meibos

(57) ABSTRACT

Inserters for dynamic implants include hooks that engage connecting means of the implants and rams that press against bridges of the implants when the inserters are actuated.

6 Claims, 13 Drawing Sheets

(56) References Cited

U.S. PATENT DOCUMENTS

| | | | |
|---|---|---|---|
| 4,874,122 | A | 10/1989 | Froelich |
| 5,013,315 | A | 5/1991 | Barrows |
| 5,044,540 | A | 9/1991 | Dulebohn |
| 5,209,756 | A | 5/1993 | Seedhom |
| 5,246,443 | A | 9/1993 | Mai |
| 5,258,012 | A | 11/1993 | Luscombe |
| 5,352,229 | A | 10/1994 | Goble |
| 5,395,372 | A | 3/1995 | Holt |
| 5,425,489 | A * | 6/1995 | Shichman .......... A61B 17/0643 227/108 |
| 5,449,359 | A | 9/1995 | Groiso |
| 5,454,814 | A | 10/1995 | Comte |
| 5,456,400 | A | 10/1995 | Shichman |
| 5,490,409 | A | 2/1996 | Weber |
| 5,498,749 | A | 3/1996 | Heise |
| 5,520,700 | A | 5/1996 | Beyar |
| 5,578,034 | A | 11/1996 | Estes |
| 5,607,425 | A | 3/1997 | Rogozinski |
| 5,628,740 | A | 5/1997 | Mullane |
| 5,634,926 | A | 6/1997 | Jobe |
| 5,660,188 | A | 8/1997 | Groiso |
| 5,662,655 | A | 9/1997 | Laboureau |
| 5,716,357 | A | 2/1998 | Rogozinski |
| 5,749,564 | A | 5/1998 | Malek |
| 5,779,707 | A | 7/1998 | Bertholet |
| 5,785,713 | A | 7/1998 | Jobe |
| 5,788,698 | A | 8/1998 | Savornin |
| 5,807,403 | A | 9/1998 | Beyar |
| 5,853,414 | A | 12/1998 | Groiso |
| 5,904,682 | A | 5/1999 | Rogozinski |
| 5,931,839 | A | 8/1999 | Medoff |
| 5,947,968 | A | 9/1999 | Rogozinski |
| 5,947,999 | A | 9/1999 | Groiso |
| 5,972,000 | A | 10/1999 | Beyar |
| 5,993,476 | A | 11/1999 | Groiso |
| 6,010,504 | A | 1/2000 | Rogozinski |
| 6,017,343 | A | 1/2000 | Rogozinski |
| 6,019,759 | A | 2/2000 | Rogozinski |
| 6,059,787 | A | 5/2000 | Allen |
| 6,089,435 | A | 7/2000 | Malek |
| 6,105,936 | A | 8/2000 | Malek |
| 6,179,840 | B1 | 1/2001 | Bowman |
| 6,187,009 | B1 | 2/2001 | Herzog |
| 6,281,262 | B1 | 8/2001 | Shikinami |
| 6,322,562 | B1 | 11/2001 | Wolter |
| 6,334,446 | B1 | 1/2002 | Beyar |
| 6,336,927 | B2 | 1/2002 | Rogozinski |
| 6,348,054 | B1 | 2/2002 | Allen |
| 6,364,884 | B1 | 4/2002 | Bowman |
| 6,379,354 | B1 | 4/2002 | Rogozinski |
| 6,387,041 | B1 | 5/2002 | Harari |
| 6,402,765 | B1 | 6/2002 | Monassevitch |
| 6,402,766 | B2 | 6/2002 | Bowman |
| 6,406,480 | B1 | 6/2002 | Beyar |
| 6,423,073 | B2 | 7/2002 | Bowman |
| 6,436,110 | B2 | 8/2002 | Bowman |
| 6,447,517 | B1 | 9/2002 | Bowman |
| 6,497,707 | B1 | 12/2002 | Bowman |
| 6,544,273 | B1 | 4/2003 | Harari |
| 6,575,984 | B2 | 6/2003 | Beyar |
| 6,575,998 | B2 | 6/2003 | Beyar |
| 6,582,435 | B2 | 6/2003 | Wellisz |
| 6,592,610 | B2 | 7/2003 | Beyar |
| 6,635,058 | B2 | 10/2003 | Beyar |
| 6,652,531 | B2 | 11/2003 | Wellisz |
| 6,663,642 | B2 | 12/2003 | Beyar |
| 6,679,885 | B2 | 1/2004 | Wellisz |
| 6,709,437 | B2 | 3/2004 | Wellisz |
| 6,730,110 | B1 | 5/2004 | Harari |
| 6,746,455 | B2 | 6/2004 | Beyar |
| 6,783,531 | B2 | 8/2004 | Allen |
| 6,896,684 | B2 | 5/2005 | Monassevitch |
| 6,966,911 | B2 | 11/2005 | Groiso |
| 6,974,461 | B1 | 12/2005 | Wolter |
| 7,044,951 | B2 | 5/2006 | Medoff |
| 7,090,676 | B2 | 8/2006 | Huebner |
| 7,147,640 | B2 | 12/2006 | Huebner |
| 7,153,309 | B2 | 12/2006 | Huebner |
| 7,179,260 | B2 | 2/2007 | Gerlach |
| 7,189,237 | B2 | 3/2007 | Huebner |
| 7,214,232 | B2 | 5/2007 | Bowman |
| 7,226,408 | B2 | 6/2007 | Harai |
| 7,229,452 | B2 | 6/2007 | Kayan |
| 7,235,079 | B2 | 6/2007 | Jensen |
| 7,250,054 | B2 | 7/2007 | Allen |
| 7,255,701 | B2 | 8/2007 | Allen |
| 7,311,712 | B2 | 12/2007 | Dalton |
| 7,326,212 | B2 | 2/2008 | Huebner |
| 7,438,209 | B1 | 10/2008 | Hess |
| 7,473,255 | B2 | 1/2009 | McGarity |
| 7,473,257 | B2 | 1/2009 | Knöpfle |
| 7,500,979 | B2 | 3/2009 | Hueil |
| 7,506,791 | B2 | 3/2009 | Omaits |
| 7,537,596 | B2 | 5/2009 | Jensen |
| 7,537,603 | B2 | 5/2009 | Huebner |
| 7,537,604 | B2 | 5/2009 | Huebner |
| 7,556,647 | B2 * | 7/2009 | Drews .................. A61B 17/064 623/2.11 |
| 7,562,105 | B2 | 7/2009 | Liu |
| 7,578,825 | B2 | 8/2009 | Huebner |
| 7,604,151 | B2 | 10/2009 | Hess |
| 7,618,441 | B2 | 11/2009 | Groiso |
| 7,651,498 | B2 | 1/2010 | Shifrin |
| 7,665,647 | B2 | 2/2010 | Shelton, IV |
| 7,669,746 | B2 | 3/2010 | Shelton, IV |
| 7,669,747 | B2 | 3/2010 | Weisenburgh, II |
| 7,673,781 | B2 | 3/2010 | Swayze |
| 7,673,782 | B2 | 3/2010 | Hess |
| 7,704,251 | B2 | 4/2010 | Huebner |
| 7,704,279 | B2 | 4/2010 | Moskowitz |
| 7,717,945 | B2 | 5/2010 | Jensen |
| 7,735,703 | B2 | 6/2010 | Morgan |
| 7,740,634 | B2 | 6/2010 | Orbay |
| 7,766,209 | B2 | 8/2010 | Baxter, III |
| 7,766,948 | B1 | 8/2010 | Leung |
| 7,771,433 | B2 | 8/2010 | Orbay |
| 7,794,475 | B2 | 9/2010 | Hess |
| 7,832,612 | B2 | 11/2010 | Baxter, III |
| 7,846,188 | B2 | 12/2010 | Moskowitz |
| 7,857,186 | B2 | 12/2010 | Baxter, III |
| 7,857,836 | B2 | 12/2010 | Huebner |
| 7,867,265 | B2 | 1/2011 | Beutter |
| 7,905,381 | B2 | 3/2011 | Baxter, III |
| 7,905,910 | B2 | 3/2011 | Gerlach |
| 7,909,858 | B2 | 3/2011 | Gerlach |
| 7,914,532 | B2 | 3/2011 | Shaver |
| 7,918,879 | B2 | 4/2011 | Yeung |
| 7,927,332 | B2 | 4/2011 | Huebner |
| 7,934,630 | B2 | 5/2011 | Shelton, IV |
| 7,935,126 | B2 | 5/2011 | Orbay |
| 7,942,903 | B2 | 5/2011 | Moskowitz |
| 7,951,180 | B2 | 5/2011 | Moskowitz |
| 7,954,686 | B2 | 6/2011 | Baxter, III |
| 7,955,388 | B2 | 6/2011 | Jensen |
| 7,963,982 | B2 | 6/2011 | Kirschman |
| 7,966,799 | B2 | 6/2011 | Morgan |
| 7,972,363 | B2 | 7/2011 | Moskowitz |
| 8,016,867 | B2 | 9/2011 | Bowman |
| 8,043,346 | B2 | 10/2011 | Markworth |
| 8,100,953 | B2 | 1/2012 | White |
| 8,105,367 | B2 | 1/2012 | Austin |
| 8,114,139 | B2 | 2/2012 | Sournac |
| 8,137,351 | B2 | 3/2012 | Prandi |
| 8,141,762 | B2 | 3/2012 | Bedi |
| 8,172,886 | B2 | 5/2012 | Castaneda |
| 8,177,819 | B2 | 5/2012 | Huebner |
| 8,182,518 | B2 | 5/2012 | Butler |
| 8,186,560 | B2 | 5/2012 | Hess |
| 8,205,781 | B2 | 6/2012 | Baxter, III |
| 8,220,690 | B2 | 7/2012 | Hess |
| 8,231,627 | B2 | 7/2012 | Huebner |
| 8,231,662 | B2 | 7/2012 | Huebner |
| 8,241,326 | B2 | 8/2012 | Harari |
| 8,241,338 | B2 | 8/2012 | Castaneda |

(56) References Cited

U.S. PATENT DOCUMENTS

| | | |
|---|---|---|
| 8,252,032 B2 | 8/2012 | White |
| 8,257,370 B2 | 9/2012 | Moskowitz |
| 8,262,711 B2 | 9/2012 | Hess |
| 8,287,543 B2 | 10/2012 | Medoff |
| 8,317,070 B2 | 11/2012 | Hueil |
| 8,337,537 B2 | 12/2012 | Pelo |
| 8,348,129 B2 | 1/2013 | Bedi |
| 8,348,131 B2 | 1/2013 | Omaits |
| 8,353,913 B2 | 1/2013 | Moskowitz |
| 8,360,297 B2 | 1/2013 | Shelton, IV |
| 8,365,976 B2 | 2/2013 | Hess |
| 8,382,807 B2 | 2/2013 | Austin |
| 8,393,517 B2 | 3/2013 | Milo |
| 8,398,717 B2 | 3/2013 | Kleinman |
| 8,413,872 B2 | 4/2013 | Patel |
| 8,425,574 B2 | 4/2013 | Huebner |
| 8,425,575 B2 | 4/2013 | Huebner |
| 8,425,576 B2 | 4/2013 | Anderson |
| 8,430,292 B2 | 4/2013 | Patel |
| 8,449,561 B2 | 5/2013 | Bowman |
| 8,453,908 B2 | 6/2013 | Bedi |
| 8,464,923 B2 | 6/2013 | Shelton, IV |
| 8,475,504 B2 | 7/2013 | Gillard |
| 8,485,412 B2 | 7/2013 | Shelton, IV |
| 8,486,116 B2 | 7/2013 | Heilman |
| 8,496,693 B2 | 7/2013 | Robinson |
| 8,499,993 B2 | 8/2013 | Shelton, IV |
| 8,518,090 B2 | 8/2013 | Huebner |
| 8,523,919 B2 | 9/2013 | Huebner |
| 8,540,129 B2 | 9/2013 | Baxter, III |
| 8,540,133 B2 | 9/2013 | Bedi |
| 8,545,540 B2 | 10/2013 | Castaneda |
| 8,561,870 B2 | 10/2013 | Baxter, III |
| 8,567,656 B2 | 10/2013 | Shelton, IV |
| 8,574,270 B2 | 11/2013 | Hess |
| 8,584,853 B2 | 11/2013 | Knight |
| 8,585,743 B2 | 11/2013 | Ampuero |
| 8,590,762 B2 | 11/2013 | Hess |
| 8,596,514 B2 | 12/2013 | Miller |
| 8,603,161 B2 | 12/2013 | Drews |
| 8,636,187 B2 | 1/2014 | Hueil |
| 8,652,142 B2 | 2/2014 | Geissler |
| 8,652,180 B2 | 2/2014 | Federspiel |
| 8,657,820 B2 | 2/2014 | Kubiak |
| 8,668,130 B2 | 3/2014 | Hess |
| 8,672,208 B2 | 3/2014 | Hess |
| 8,672,828 B2 | 3/2014 | Harari |
| 8,679,123 B2 | 3/2014 | Kinmon |
| 8,720,766 B2 | 5/2014 | Hess |
| 8,727,197 B2 | 5/2014 | Hess |
| 8,728,128 B2 | 5/2014 | Hawkes |
| 8,728,129 B2 | 5/2014 | Fritzinger |
| 8,734,516 B2 | 5/2014 | Moskowitz |
| 8,740,915 B2 | 6/2014 | Niederberger |
| 8,747,444 B2 | 6/2014 | Moskowitz |
| 8,763,875 B2 | 7/2014 | Morgan |
| 8,777,969 B2 | 7/2014 | Kayan |
| 8,779,927 B2 | 7/2014 | Bell |
| 8,784,450 B2 | 7/2014 | Moskowitz |
| 8,800,838 B2 | 8/2014 | Shelton, IV |
| 8,808,325 B2 | 8/2014 | Hess |
| 8,814,915 B2 | 8/2014 | Hess |
| 8,834,537 B2 | 9/2014 | Castaneda |
| 8,858,562 B2 | 10/2014 | Orbay |
| 8,870,882 B2 | 10/2014 | Kleiner |
| 8,882,812 B2 | 11/2014 | Hess |
| 8,888,824 B2 | 11/2014 | Austin |
| 8,888,826 B2 | 11/2014 | Kinmon |
| 8,894,651 B2 | 11/2014 | Aflatoon |
| 8,899,465 B2 | 12/2014 | Shelton, IV |
| 8,906,046 B2 | 12/2014 | Anderson |
| 8,925,788 B2 | 1/2015 | Hess |
| 8,940,028 B2 | 1/2015 | Austin |
| 8,973,804 B2 | 3/2015 | Hess |
| 8,974,504 B2 | 3/2015 | Hess |
| 8,986,305 B2 | 3/2015 | Aflatoon |
| 8,991,676 B2 | 3/2015 | Hess |
| 8,992,581 B2 | 3/2015 | Austin |
| 9,005,206 B2 | 4/2015 | Ampuero |
| 9,005,293 B2 | 4/2015 | Moskowitz |
| 9,017,331 B2 | 4/2015 | Fox |
| 9,017,380 B2 | 4/2015 | Mayer |
| 9,034,037 B2 | 5/2015 | Fiere |
| 9,072,554 B2 | 7/2015 | Reynolds |
| 9,078,757 B2 | 7/2015 | Kleinman |
| 9,095,338 B2 | 8/2015 | Taylor |
| 9,095,388 B2 | 8/2015 | Hess |
| 9,101,349 B2 | 8/2015 | Knight |
| 9,107,661 B2 | 8/2015 | Euteneuer |
| 9,125,650 B2 | 9/2015 | Euteneuer |
| 9,138,233 B2 | 9/2015 | Anderson |
| 9,179,911 B2 | 11/2015 | Morgan |
| 9,180,022 B2 | 11/2015 | Georges |
| 9,204,932 B2 | 12/2015 | Knight |
| 9,220,515 B2 | 12/2015 | Castaneda |
| 9,237,891 B2 | 1/2016 | Shelton, IV |
| 9,247,978 B2 | 2/2016 | Euteneuer |
| 9,265,649 B2 | 2/2016 | Pflueger |
| 752,219 A1 | 3/2016 | Peterson |
| 9,271,726 B2 | 3/2016 | Euteneuer |
| 9,283,006 B2 | 3/2016 | Fonte |
| 9,289,206 B2 | 3/2016 | Hess |
| 9,289,210 B2 | 3/2016 | Baxter, III |
| 9,301,854 B2 | 4/2016 | Moskowitz |
| 9,307,988 B2 | 4/2016 | Shelton, IV |
| 9,308,033 B2 | 4/2016 | Huebner |
| 9,326,768 B2 | 5/2016 | Shelton, IV |
| 9,326,771 B2 | 5/2016 | Baxter, III |
| 9,339,268 B2 | 5/2016 | Fox |
| 9,370,355 B2 | 6/2016 | Anderson |
| 9,370,356 B2 | 6/2016 | Euteneuer |
| 9,370,376 B2 | 6/2016 | Castaneda |
| 9,387,116 B2 | 7/2016 | Pflueger |
| 9,402,623 B2 | 8/2016 | Kayan |
| 9,402,624 B1 | 8/2016 | Scott |
| 9,408,603 B2 | 8/2016 | Patel |
| 9,408,604 B2 | 8/2016 | Shelton, IV |
| 9,414,841 B2 | 8/2016 | Euteneuer |
| 9,414,871 B2 | 8/2016 | Huebner |
| 9,421,013 B2 | 8/2016 | Patel |
| 9,445,808 B2 | 9/2016 | Woodard, Jr. |
| 9,451,957 B2 | 9/2016 | Fox |
| 9,463,015 B2 | 10/2016 | Hausen |
| 9,486,212 B2 | 11/2016 | Miller |
| 9,532,821 B2 | 1/2017 | Moskowitz |
| 9,539,023 B2 | 1/2017 | Marotte |
| 9,549,735 B2 | 1/2017 | Shelton, IV |
| 9,561,032 B2 | 2/2017 | Shelton, IV |
| 9,566,063 B2 | 2/2017 | Euteneuer |
| 9,603,641 B2 | 3/2017 | Hulliger |
| 9,615,856 B2 | 4/2017 | Arnett |
| 9,763,715 B2 | 9/2017 | Mather |
| 9,918,762 B2 | 3/2018 | Federspiel |
| 9,924,984 B2 | 3/2018 | Hartdegen |
| 9,955,964 B2 | 5/2018 | Mayer |
| 10,052,103 B2 * | 8/2018 | Wahl ................ A61B 17/0682 |
| 10,166,022 B2 | 1/2019 | Early |
| 10,186,402 B2 | 1/2019 | Kamata |
| 10,357,986 B2 | 7/2019 | Zhou |
| 10,492,841 B2 | 12/2019 | Hartdegen |
| 2001/0028148 A1 | 10/2001 | White |
| 2002/0095181 A1 | 7/2002 | Beyar |
| 2002/0111641 A1 | 8/2002 | Peterson |
| 2003/0083663 A1 | 5/2003 | Goldhahn |
| 2003/0158553 A1 | 8/2003 | Michelson |
| 2003/0225409 A1 | 12/2003 | Freid |
| 2004/0073222 A1 | 4/2004 | Koseki |
| 2004/0127896 A1 | 7/2004 | Lombardo |
| 2004/0172040 A1 | 9/2004 | Heggeness |
| 2004/0220570 A1 | 11/2004 | Frigg |
| 2005/0021032 A1 | 1/2005 | Koo |
| 2005/0021035 A1 | 1/2005 | Groiso |
| 2005/0043757 A1 | 2/2005 | Arad |
| 2005/0049600 A1 | 3/2005 | Groiso |

(56) References Cited

U.S. PATENT DOCUMENTS

| | | |
|---|---|---|
| 2005/0085818 A1 | 4/2005 | Huebner |
| 2005/0096660 A1 | 5/2005 | Allen |
| 2005/0101961 A1 | 5/2005 | Huebner |
| 2005/0107796 A1 | 5/2005 | Gerlach |
| 2005/0119667 A1 | 6/2005 | Leport |
| 2005/0165400 A1 | 7/2005 | Fernandez |
| 2005/0171544 A1 | 8/2005 | Falkner |
| 2005/0234458 A1 | 10/2005 | Huebner |
| 2005/0240187 A1 | 10/2005 | Huebner |
| 2006/0058796 A1 | 3/2006 | Hartdegen |
| 2006/0058802 A1 | 3/2006 | Kofoed |
| 2006/0106391 A1 | 5/2006 | Huebner |
| 2006/0122604 A1 | 6/2006 | Gorhan |
| 2006/0122605 A1 | 6/2006 | Suh |
| 2006/0129151 A1 | 6/2006 | Allen |
| 2006/0200147 A1 | 9/2006 | Ensign |
| 2006/0241612 A1 | 10/2006 | Medoff |
| 2006/0241618 A1 | 10/2006 | Gasser |
| 2006/0264936 A1 | 11/2006 | Partin |
| 2007/0055249 A1 | 3/2007 | Jensen |
| 2007/0173840 A1 | 7/2007 | Huebner |
| 2007/0191850 A1 | 8/2007 | Kim |
| 2007/0208358 A1 | 9/2007 | Kayan |
| 2007/0233116 A1 | 10/2007 | Olerud |
| 2008/0147125 A1 | 6/2008 | Colleran |
| 2008/0195099 A1 | 8/2008 | Minas |
| 2008/0200955 A1 | 8/2008 | Tepic |
| 2008/0255620 A1 | 10/2008 | Strauss |
| 2008/0275510 A1 | 11/2008 | Schonhardt |
| 2008/0288000 A1 | 11/2008 | Cawley |
| 2008/0319443 A1 | 12/2008 | Focht |
| 2009/0054930 A1 | 2/2009 | Aflatoon |
| 2009/0138082 A1 | 5/2009 | Reah |
| 2009/0177203 A1 | 7/2009 | Reiley |
| 2009/0182383 A1 | 7/2009 | Prybyla |
| 2009/0254090 A1 | 10/2009 | Lizee |
| 2009/0254126 A1 | 10/2009 | Orbay |
| 2009/0281543 A1 | 11/2009 | Orbay |
| 2010/0036430 A1 | 2/2010 | Hartdegen |
| 2010/0076448 A1 | 3/2010 | Abdou |
| 2010/0082065 A1 | 4/2010 | Butler |
| 2010/0100138 A1 | 4/2010 | Reynolds |
| 2010/0106196 A1 | 4/2010 | Erickson |
| 2010/0133316 A1 | 6/2010 | Lizee |
| 2010/0211116 A1 | 8/2010 | Suh |
| 2010/0256765 A1 | 10/2010 | Butler |
| 2010/0292715 A1 | 11/2010 | Nering |
| 2010/0312280 A1 | 12/2010 | Overes |
| 2011/0022049 A1 | 1/2011 | Huebner |
| 2011/0022099 A1 | 1/2011 | Ashman |
| 2011/0029016 A1 | 2/2011 | Yeung |
| 2011/0029023 A1 | 2/2011 | Tornier |
| 2011/0029025 A1 | 2/2011 | Medoff |
| 2011/0054542 A1 | 3/2011 | Kevin |
| 2011/0092981 A1 | 4/2011 | Ng |
| 2011/0098754 A1 | 4/2011 | Hulliger |
| 2011/0118796 A1 | 5/2011 | Reiley |
| 2011/0118840 A1 | 5/2011 | Huntsman |
| 2011/0202092 A1 | 8/2011 | Frigg |
| 2011/0270326 A1 | 11/2011 | Black |
| 2011/0282393 A1 | 11/2011 | Gerlach |
| 2011/0295324 A1 | 12/2011 | Donley |
| 2011/0313421 A1 | 12/2011 | Sidebotham |
| 2011/0319942 A1 | 12/2011 | Bottlang |
| 2012/0022600 A1 | 1/2012 | Overes |
| 2012/0024937 A1 | 2/2012 | Allen |
| 2012/0053638 A1 | 3/2012 | Rusch |
| 2012/0059425 A1 | 3/2012 | Biedermann |
| 2012/0065690 A1 | 3/2012 | Perrow |
| 2012/0078371 A1 | 3/2012 | Gamache |
| 2012/0095513 A1 | 4/2012 | Humphreys |
| 2012/0130374 A1 | 5/2012 | Bouduban |
| 2012/0136396 A1 | 5/2012 | Baker |
| 2012/0143193 A1 | 6/2012 | Hulliger |
| 2012/0150240 A1 | 6/2012 | Medoff |
| 2012/0179207 A1 | 7/2012 | Mekhail |
| 2012/0191141 A1 | 7/2012 | Costabile |
| 2012/0323284 A1 | 12/2012 | Baker |
| 2013/0006247 A1 | 1/2013 | Weiner |
| 2013/0023938 A1 | 1/2013 | Huebner |
| 2013/0023940 A1 | 1/2013 | Hansell |
| 2013/0026206 A1 | 1/2013 | Fox |
| 2013/0030437 A1 | 1/2013 | Fox |
| 2013/0046346 A1 | 2/2013 | Thorwarth |
| 2013/0109910 A1 | 5/2013 | Alexander |
| 2013/0138154 A1 | 5/2013 | Reiley |
| 2013/0150900 A1 | 6/2013 | Haddad |
| 2013/0218285 A1 | 8/2013 | Kleinman |
| 2013/0226252 A1 | 8/2013 | Mayer |
| 2013/0231667 A1 | 9/2013 | Taylor |
| 2013/0238035 A1 | 9/2013 | Medoff |
| 2013/0267956 A1 | 10/2013 | Terrill |
| 2013/0303071 A1 | 11/2013 | Seki |
| 2013/0325074 A1 | 12/2013 | Ziolo |
| 2013/0345752 A1 | 12/2013 | Hendren |
| 2014/0014553 A1 | 1/2014 | Knight |
| 2014/0018809 A1 | 1/2014 | Allen |
| 2014/0018862 A1 | 1/2014 | Koay |
| 2014/0020333 A1 | 1/2014 | Knight |
| 2014/0024002 A1 | 1/2014 | Knight |
| 2014/0034702 A1 | 2/2014 | Miller |
| 2014/0058461 A1 | 2/2014 | Black |
| 2014/0100652 A1 | 4/2014 | Drews |
| 2014/0142628 A1 | 5/2014 | Traynelis |
| 2014/0163621 A1 | 6/2014 | Huebner |
| 2014/0163682 A1 | 6/2014 | Iott |
| 2014/0163683 A1 | 6/2014 | Seifert |
| 2014/0172026 A1 | 6/2014 | Biedermann |
| 2014/0200670 A1 | 7/2014 | Chin |
| 2014/0207195 A1 | 7/2014 | Appenzeller |
| 2014/0222086 A1 | 8/2014 | Kuster |
| 2014/0257420 A1 | 9/2014 | Fox |
| 2014/0276830 A1 | 9/2014 | Cheney |
| 2014/0296925 A1 | 10/2014 | Lawson |
| 2014/0309639 A1 | 10/2014 | Averous |
| 2014/0316470 A1 | 10/2014 | Hartdegen |
| 2014/0358187 A1 | 12/2014 | Taber |
| 2015/0012003 A1 | 1/2015 | Ryan |
| 2015/0045804 A1 | 2/2015 | Orbay |
| 2015/0066095 A1 | 3/2015 | Austin |
| 2015/0080914 A1 | 3/2015 | Roundy |
| 2015/0080969 A1 | 3/2015 | Holly |
| 2015/0133940 A1 | 5/2015 | Palmer |
| 2015/0142063 A1 | 5/2015 | Austin |
| 2015/0148850 A1 | 5/2015 | Orbay |
| 2015/0164564 A1 | 6/2015 | Reiley |
| 2015/0173749 A1 | 6/2015 | Shelton, IV |
| 2015/0173750 A1 | 6/2015 | Shelton, IV |
| 2015/0173751 A1 | 6/2015 | Shelton, IV |
| 2015/0173756 A1 | 6/2015 | Baxter, III |
| 2015/0196333 A1 | 7/2015 | Austin |
| 2015/0216570 A1 | 8/2015 | Hess |
| 2015/0216573 A1 | 8/2015 | Chin |
| 2015/0238191 A1 | 8/2015 | Schellin |
| 2015/0238238 A1 | 8/2015 | Cheney |
| 2015/0282819 A1 | 10/2015 | Austin |
| 2015/0313592 A1 | 11/2015 | Coillard-Lavirotte |
| 2015/0320462 A1 | 11/2015 | Biedermann |
| 2015/0351762 A1 | 12/2015 | Vendely |
| 2015/0351763 A1 | 12/2015 | Shelton, IV |
| 2015/0351764 A1 | 12/2015 | Shelton, IV |
| 2016/0015384 A1 | 1/2016 | Roedl |
| 2016/0066907 A1 | 3/2016 | Cheney |
| 2016/0074037 A1 | 3/2016 | Cheney |
| 2016/0089191 A1 | 3/2016 | Pak |
| 2016/0100835 A1 | 4/2016 | Linder |
| 2016/0157906 A1 | 6/2016 | Hollis |
| 2016/0192930 A1 | 7/2016 | Finley |
| 2016/0199060 A1* | 7/2016 | Morgan .............. A61B 17/068 227/175.1 |
| 2016/0235460 A1 | 8/2016 | Wahl |
| 2016/0242771 A1 | 8/2016 | Weinstein |
| 2016/0242927 A1 | 8/2016 | Seifert |
| 2016/0338697 A1* | 11/2016 | Biedermann ...... A61B 17/0682 |

(56) References Cited

U.S. PATENT DOCUMENTS

| | | |
|---|---|---|
| 2016/0354117 A1 | 12/2016 | Nakaji |
| 2017/0000482 A1* | 1/2017 | Averous ............ A61B 17/0642 |
| 2017/0000533 A1 | 1/2017 | Fallin |
| 2017/0007305 A1 | 1/2017 | Hollis |
| 2017/0065276 A1 | 3/2017 | Weiner |
| 2017/0065312 A1 | 3/2017 | Lauf |
| 2017/0112553 A1 | 4/2017 | Hansell |
| 2017/0119443 A1 | 5/2017 | Cawley |
| 2017/0156776 A1 | 6/2017 | Weiman |
| 2017/0164990 A1 | 6/2017 | Weiner |
| 2017/0181779 A1 | 6/2017 | Leither |
| 2017/0196604 A1 | 7/2017 | Hartdegen |
| 2017/0196606 A1 | 7/2017 | Cianfrani |
| 2017/0202552 A1 | 7/2017 | Coleman |
| 2017/0202585 A1 | 7/2017 | Leak |
| 2017/0209193 A1 | 7/2017 | Hartdegen |
| 2017/0231625 A1* | 8/2017 | Handie ............... A61B 17/0642 227/175.1 |
| 2017/0238974 A1 | 8/2017 | Konieczynski |
| 2017/0245901 A1 | 8/2017 | Grigorian |
| 2017/0281157 A1* | 10/2017 | Hartdegen ......... A61B 17/8052 |
| 2017/0354509 A1 | 12/2017 | Finley |
| 2018/0000592 A1 | 1/2018 | Mayer |
| 2018/0206892 A1 | 7/2018 | Hartdegen |
| 2018/0296257 A1 | 10/2018 | Penzimer |
| 2018/0353172 A1 | 12/2018 | Hartdegen |
| 2019/0000451 A1 | 1/2019 | Majors |
| 2019/0150921 A1* | 5/2019 | Fonte ................. A61B 17/0642 |
| 2020/0000464 A1 | 1/2020 | Gaston |
| 2020/0000465 A1 | 1/2020 | MacLure |
| 2020/0008807 A1* | 1/2020 | Hollis ................. A61B 17/0644 |

FOREIGN PATENT DOCUMENTS

| | | |
|---|---|---|
| DE | 3119550 | 12/1982 |
| DE | 29721858 | 3/1998 |
| DE | 19821680 | 8/1999 |
| DE | 20001879 | 5/2000 |
| DE | 102004015223 | 10/2005 |
| EP | 0092383 | 11/1987 |
| EP | 0253629 | 9/1994 |
| EP | 0768062 | 4/1997 |
| EP | 0826340 | 3/1998 |
| EP | 0857462 | 8/1998 |
| EP | 0682920 | 5/2000 |
| EP | 0867149 | 9/2000 |
| EP | 1870042 | 7/2009 |
| EP | 2231044 | 3/2012 |
| EP | 3082632 | 10/2016 |
| EP | 3166505 | 5/2017 |
| EP | 3166522 | 5/2017 |
| EP | 3179939 | 6/2017 |
| FR | 2628312 | 1/1994 |
| FR | 2694696 | 11/1994 |
| FR | 2725126 | 4/1997 |
| FR | 2758252 | 4/1999 |
| FR | 2874316 | 10/2006 |
| FR | 2927527 | 8/2009 |
| FR | 2874166 | 3/2012 |
| FR | 2935256 | 3/2012 |
| FR | 2980966 | 11/2013 |
| GB | 2118474 | 10/1985 |
| GB | 2471648 | 1/2012 |
| WO | WO1992017122 | 10/1992 |
| WO | WO2001056489 | 8/2001 |
| WO | WO2003071962 | 9/2003 |
| WO | WO2003068081 | 1/2008 |
| WO | WO2008007196 | 1/2008 |
| WO | WO2008129061 | 10/2008 |
| WO | WO 2009/091770 A1 * | 7/2009 |
| WO | WO2010004602 | 1/2010 |
| WO | WO2011014547 | 2/2011 |
| WO | WO2011110916 | 9/2011 |
| WO | WO2012071129 | 5/2012 |
| WO | WO2013010282 | 1/2013 |
| WO | WO2013055824 | 4/2013 |
| WO | WO2013130978 | 9/2013 |
| WO | WO2013186205 | 12/2013 |
| WO | WO2015004391 | 1/2015 |
| WO | WO2015095126 | 6/2015 |
| WO | WO2015107311 | 7/2015 |
| WO | WO2016007624 | 1/2016 |
| WO | WO2016007626 | 1/2016 |
| WO | WO2016025162 | 2/2016 |
| WO | WO2016110760 | 7/2016 |
| WO | WO2017011589 | 1/2017 |
| WO | WO2017139315 | 8/2017 |
| WO | WO2017139328 | 8/2017 |
| WO | WO2018145064 | 8/2018 |
| WO | WO2018148284 | 8/2018 |

* cited by examiner

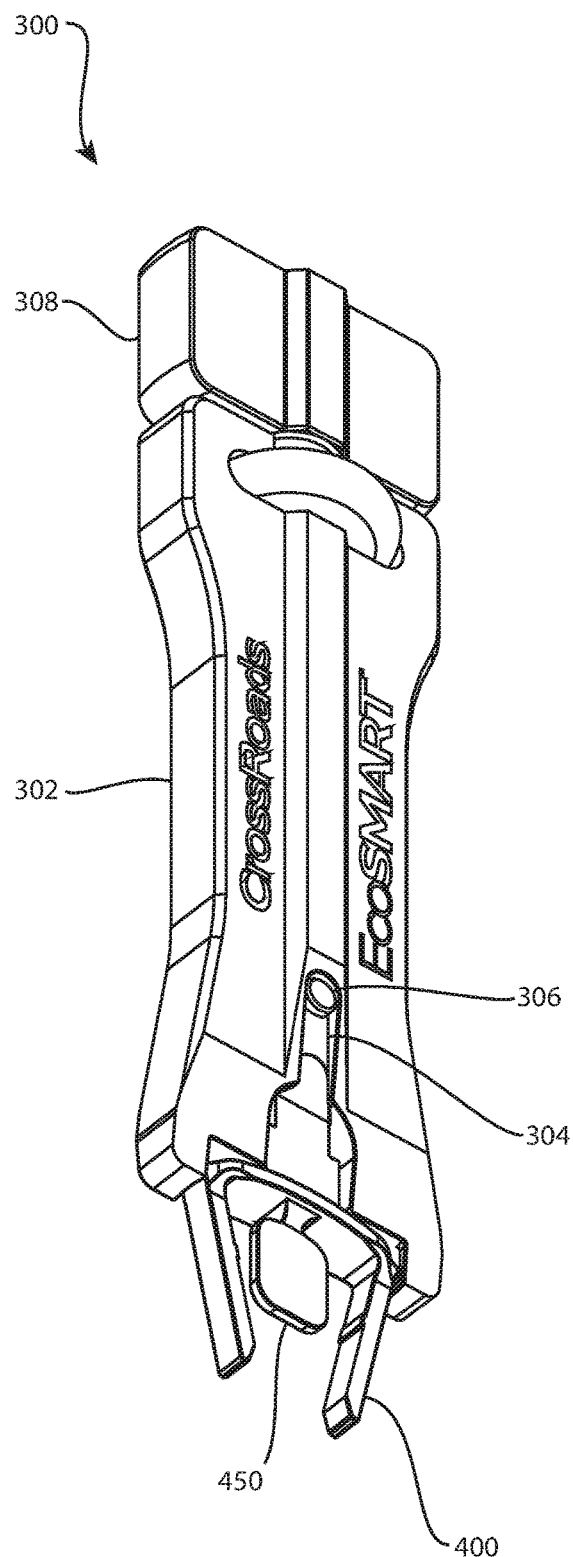
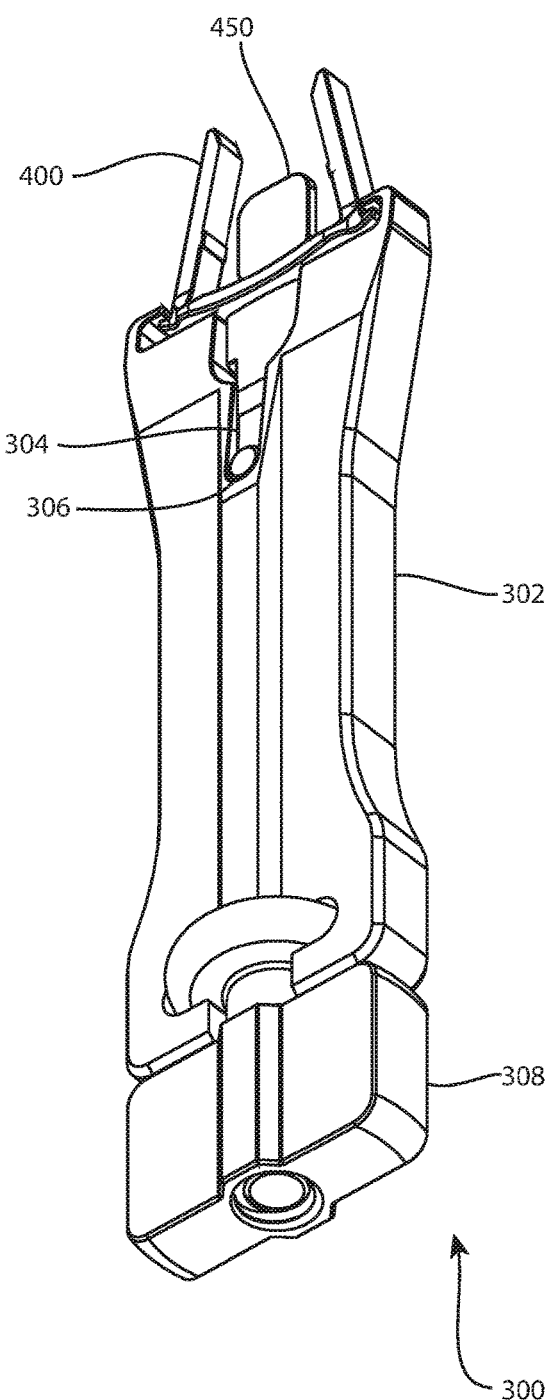
FIG. 15
FIG. 16

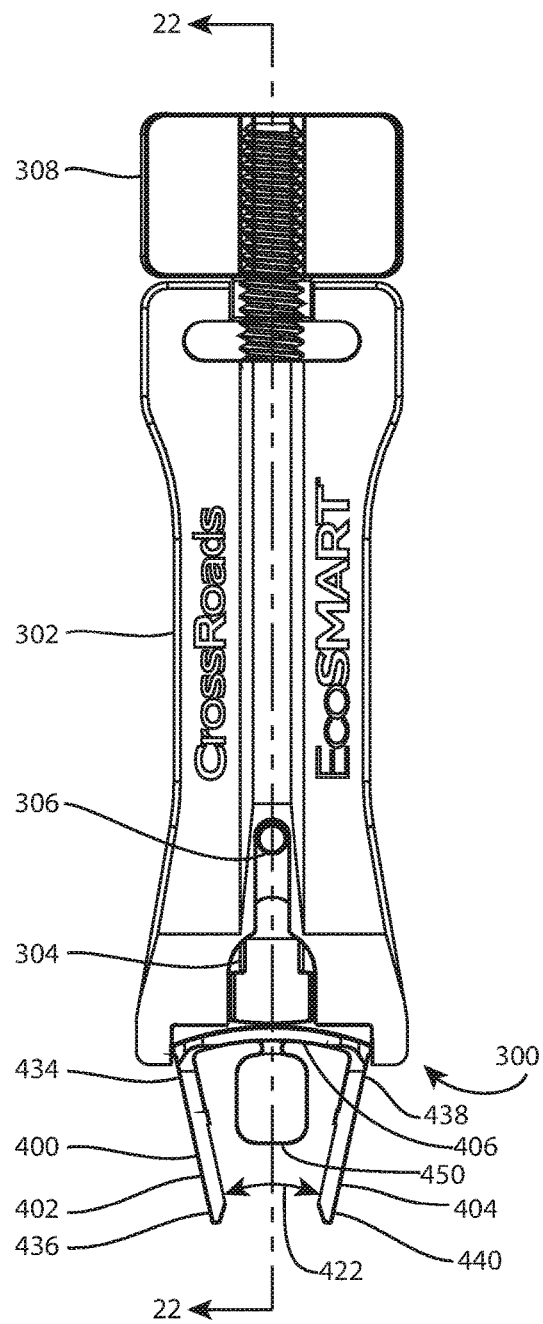
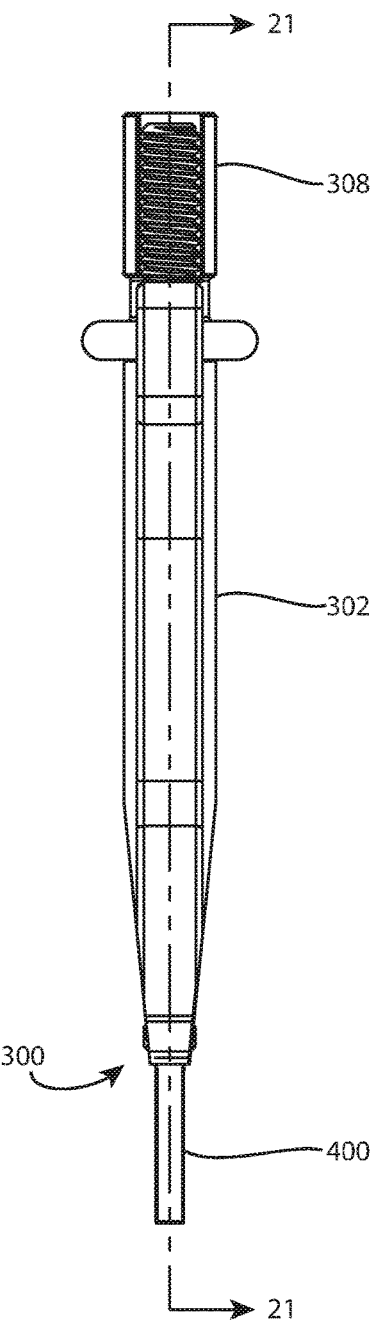
FIG. 19
FIG. 20

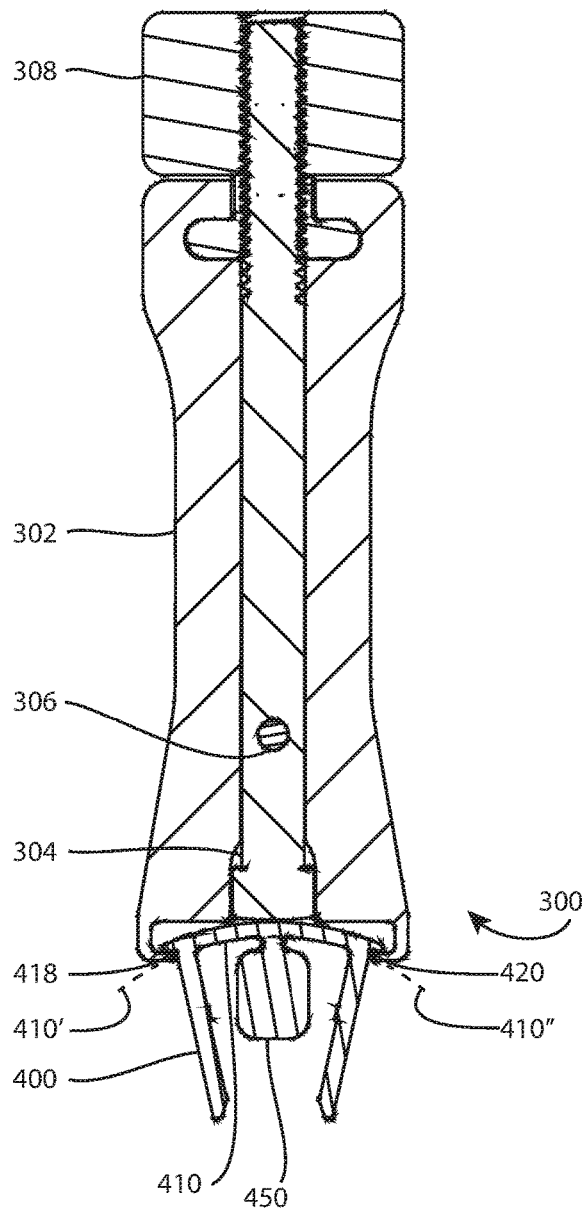
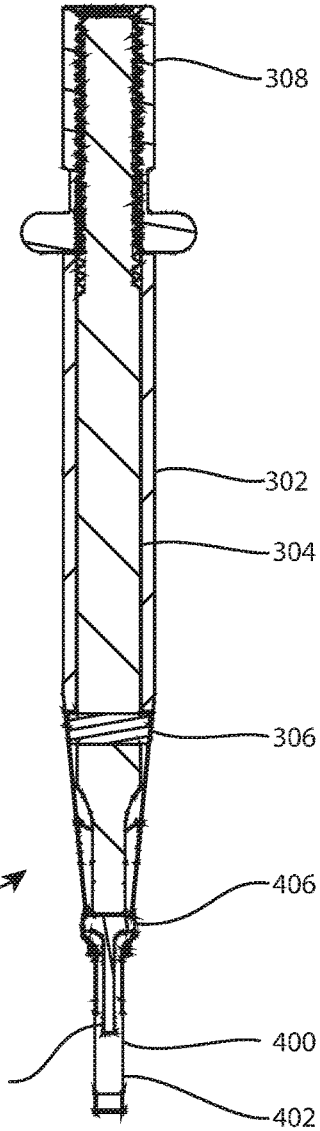
FIG. 21
FIG. 22

— 1 —

IMPLANT INSERTER

CROSS-REFERENCE TO RELATED APPLICATIONS

The present application is a continuation-in-part of International Patent Application No. PCT/US2018/016994, filed Feb. 6, 2018, entitled IMPLANT INSERTER.

International Patent Application No. PCT/US2018/016994 claims priority to:

U.S. Provisional Patent Application No. 62/455,361, filed Feb. 6, 2017, entitled IMPLANT INSERTER.

The foregoing are incorporated by reference as though set forth herein in their entirety.

TECHNICAL FIELD

The present disclosure relates to Inserters for dynamic implants. More specifically, the present disclosure relates to inserters that engage a dynamic implant bridge.

BACKGROUND

A dynamic implant has a free state, or relaxed state, which is its shape when no external forces are acting upon the implant, other than gravity perhaps. In the free state, the implant is not elastically or plastically deflected or deformed. The implant may experience loads that are below a threshold for elastic or plastic deflection or deformation. In the free state, the implant legs may converge at their distal tips. The implant may be made from high elasticity materials such as nitinol and/or polyetheretherketone (PEEK) so that the implant may be elastically deformed by an external force, and then resume the free state when the external force is removed.

The inserter securely and releasably couples to the implant. When actuated, the inserter urges the implant out of the free state into a continuum of elastically deformed states in which the implant legs may a) progressively approach a parallel condition, b) achieve a parallel condition, or c) progressively diverge at their distal tips. When the inserter is uncoupled from the implant, the implant resumes the free state, or attempts to do so. When the implant is implanted in bone, then the implant may only be able to partially relax toward the free state due to the resistance of the bone.

SUMMARY

The various systems and methods of the present technology have been developed in response to the present state of the art, and in particular, in response to the problems and needs in the art that have not yet been fully solved by currently available inserters.

To achieve the foregoing, and in accordance with the technology as embodied and broadly described herein, in an aspect of the technology, an inserter for a dynamic implant having an elongated bridge and first and second connecting means extending from first and second ends of the bridge, wherein the bridge has a proximal surface, wherein the bridge and the first and second connecting means each have a distal surface, the inserter including: first and second hooks, wherein the first and second hooks face each other across an alcove, wherein the first and second hooks each have a proximal surface, wherein the alcove has a proximal surface that is proximal to the proximal surfaces of the first and second hooks; and a ram head having a distal surface, wherein the ram head is movable relative to the first and second hooks between a proximal position and a distal position, wherein in the proximal position, the distal surface of the ram head is proximal to the proximal surface of the alcove, wherein in the distal position, the distal surface of the ram head is distal to the proximal surface of the alcove; wherein when the inserter is connected to the implant, the first and second hooks receive the first and second connecting means, the proximal surfaces of the first and second hooks contact the distal surfaces of the first and second connecting means, the alcove receives the bridge, and the distal surface of the ram head faces the proximal surface of the bridge; wherein when the inserter is connected to the implant and the ram head is in the proximal position, the implant is in a relaxed state in which the bridge is undeformed; wherein when the inserter is connected to the implant and the ram head is in the distal position, the implant is in an elastically deformed state in which the bridge is elastically deformed.

Embodiments of this aspect of the technology may include one or more of the following attributes. When the ram head moves between the proximal and distal positions, the ram head does not rotate relative to the first and second hooks. The inserter includes a ram, wherein the ram includes the ram head and a ram shaft extending proximally from, and integrally formed with, the ram head, wherein a proximal portion of the ram shaft is threaded. The inserter includes a body and a knob, wherein the knob is captive to the body. distal portion of the body includes the first and second hooks, wherein the ram shaft is received in the body, wherein the knob includes a threaded hole, wherein the proximal portion of the ram shaft threads into the knob hole, wherein the knob is captive within a slot in a proximal portion of the body. When the inserter is connected to the implant, the distal surface of the ram head contacts the proximal surface of the bridge.

In another aspect of the technology, a system for implant elastic deformation and insertion, includes: an implant movable between a relaxed state and an elastically deformed state, wherein the implant includes an elongated bridge and first and second connecting means, wherein the bridge extends between opposite first and second ends and has a distal surface and an opposite proximal surface, wherein the first connecting means extends from the first end of the bridge, wherein the second connecting means extends from the second end of the bridge, wherein each of the first and second connecting means has a distal surface, wherein when the implant is in the relaxed state, the bridge is undeformed; wherein when the implant is in the elastically deformed state, the bridge is elastically deformed; and an inserter including a ram for engaging the bridge and first and second hooks for engaging the connecting means, wherein the ram has a distal surface, wherein each of the first and second hooks has a proximal surface, wherein the first and second hooks are movable together relative to the ram between a distal position and a proximal position, wherein in the distal position, the proximal surfaces of the first and second hooks are distal to the distal surface of the ram by a first distance, wherein in the proximal position, the proximal surfaces of the first and second hooks are distal to the distal surface of the ram by a second distance, wherein the second distance is less than the first distance; wherein when the inserter is connected to the implant, the first and second hooks receive the first and second connecting means, the proximal surfaces of the first and second hooks contact the distal surfaces of the first and second connecting means, and the distal surface of the ram faces the proximal surface of the bridge; wherein when the inserter is connected to the implant and the first and second hooks are in the distal position, the implant is in the relaxed state; wherein when the inserter is connected to the implant and the first and second hooks are in the proximal position, the implant is in the elastically deformed state.

Embodiments of this aspect of the technology may include one or more of the following attributes. The ram does not rotate relative to the first and second hooks. The ram includes a proximal threaded ram shaft, wherein the distal surface of the ram is integrally formed with the ram shaft. The inserter includes a body and a knob, wherein the knob is captive to the body. A distal portion of the body includes the first and second hooks, wherein the ram shaft is received in the body, wherein the knob includes a threaded hole, wherein the ram shaft threads into the knob hole, wherein the knob is captive within a slot in a proximal portion of the body. When the inserter is connected to the implant, the distal surface of the ram contacts the proximal surface of the bridge.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 15 is a perspective view of an implant and yet another implant inserter;

FIG. 16 is another perspective view of the implant and implant inserter of FIG. 15 from a different direction;

FIG. 19 is a front view of the implant and implant inserter of FIG. 15;

FIG. 20 is a right view of the implant and implant inserter of FIG. 15;

FIG. 21 is a cross-sectional view of the implant and implant inserter of FIG. 15, taken along section line 21-21 of FIG. 20; and FIG. 22 is a cross-sectional view of the implant and implant inserter of FIG. 15, taken along section line 22-22 of FIG. 19.

DETAILED DESCRIPTION

Figure 1:
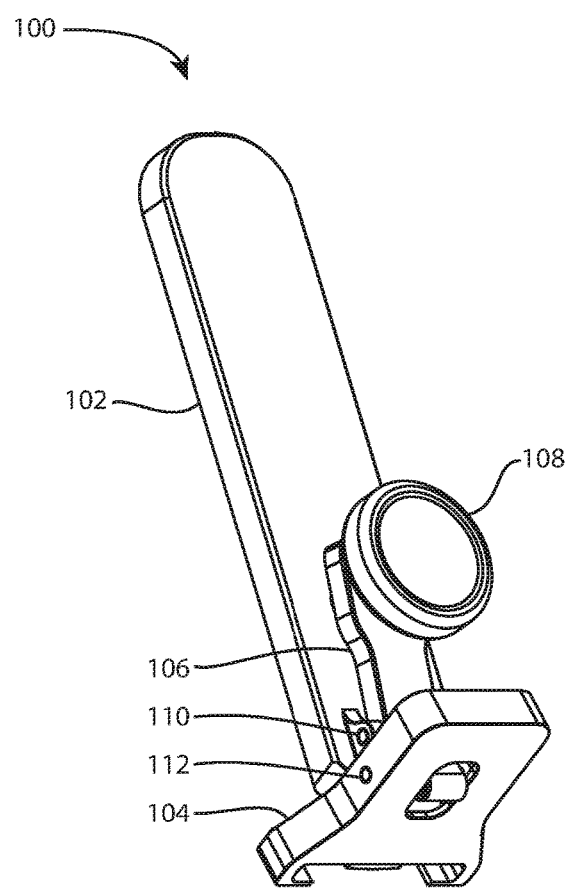
FIG. 1 is a perspective view of an implant inserter.
Figure 2:
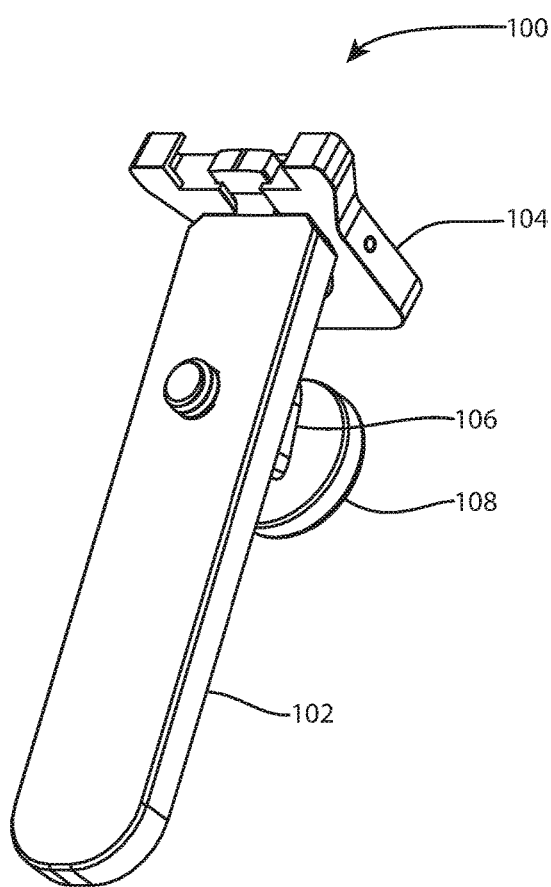
FIG. 2 is another perspective view of the implant inserter of FIG. 1 from a different direction.
Figure 3:
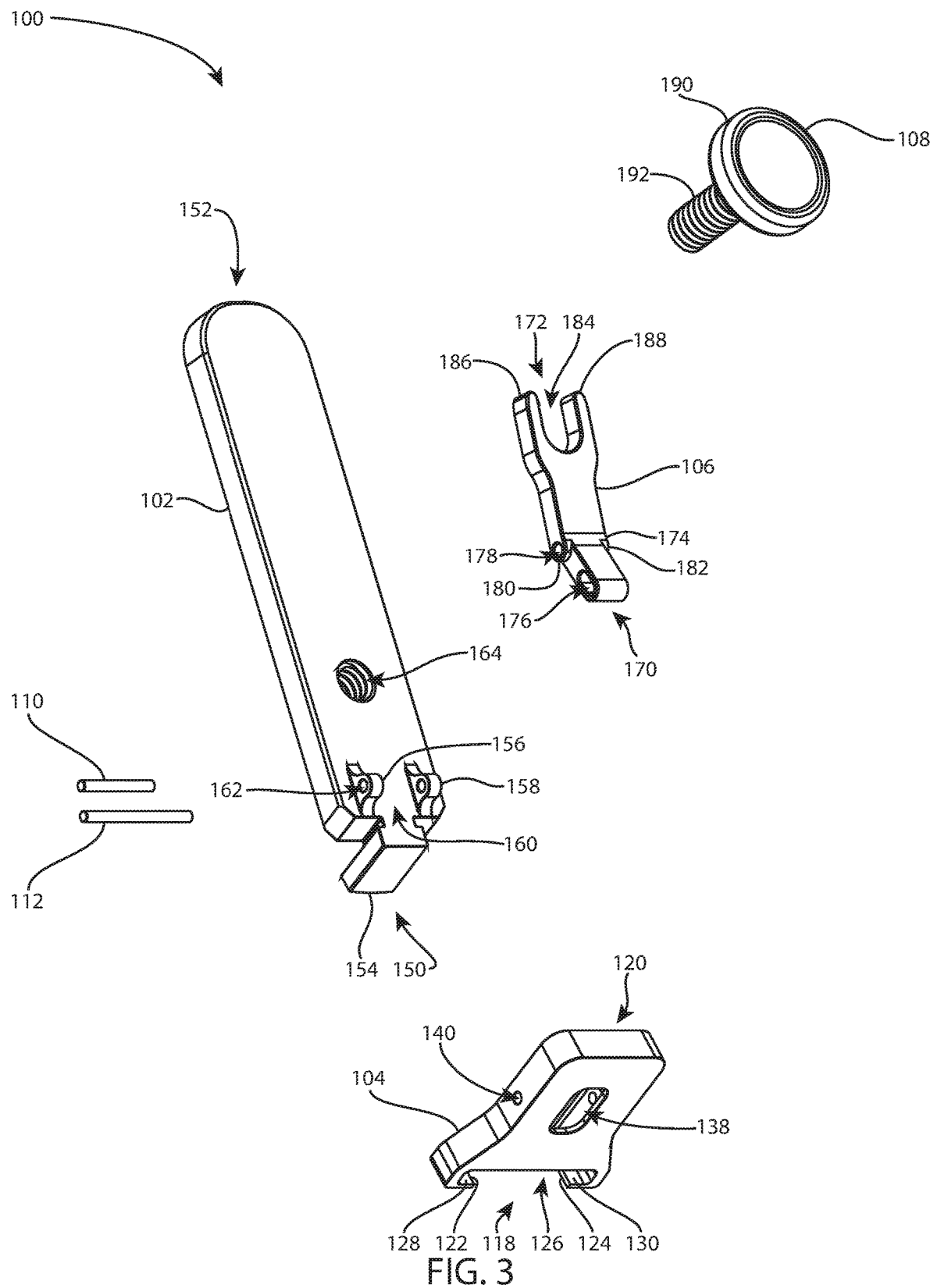
FIG. 3 is an exploded perspective view of the implant inserter of FIG. 1.
Figure 4:
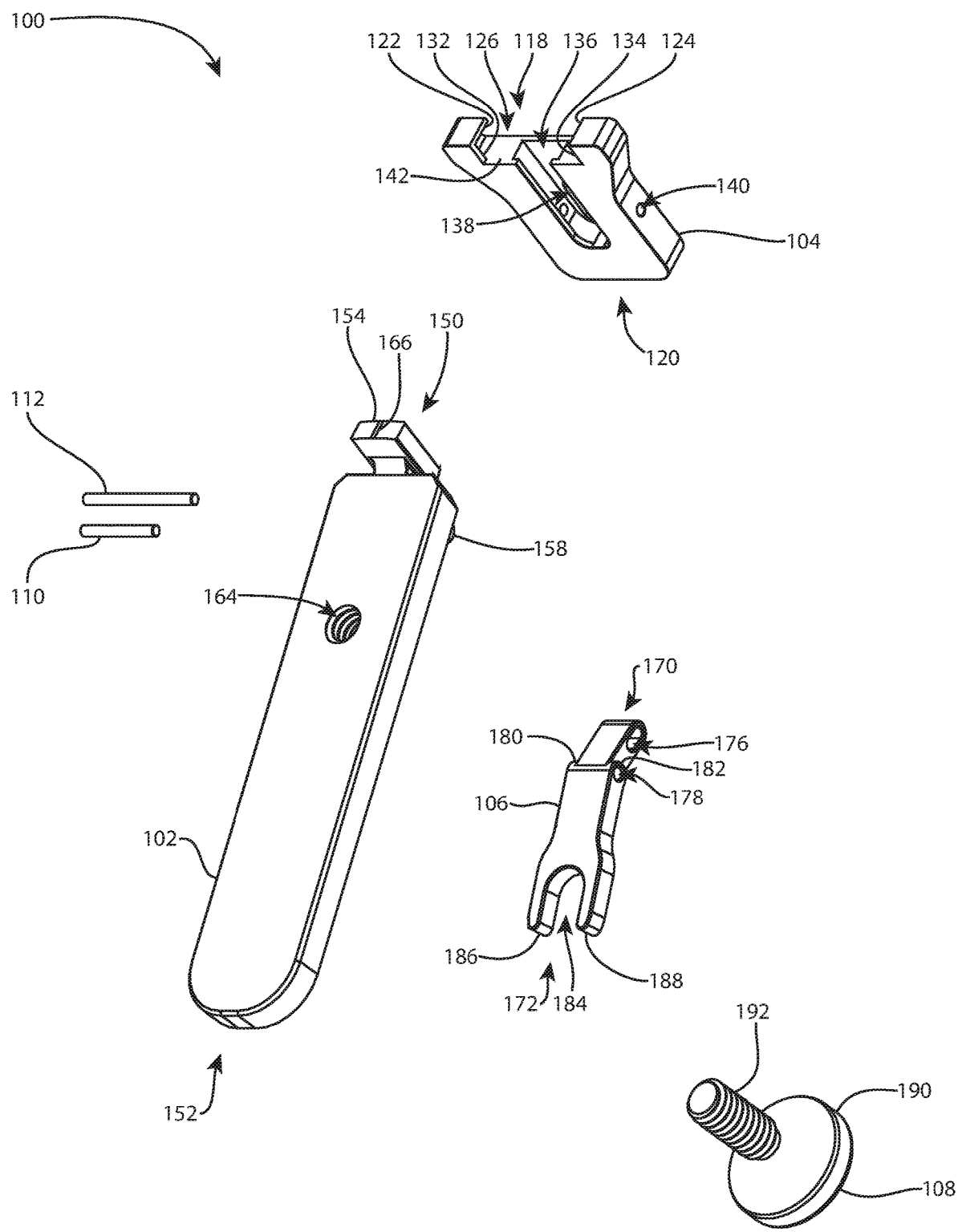
FIG. 4 is another exploded perspective view of the implant inserter of FIG. 1 from a different direction.

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot. Varus means deviation of the distal part of the leg below the knee inward, resulting in a bowlegged appearance. Valgus means deviation of the distal part of the leg below the knee outward, resulting in a knock-kneed appearance.

The implant inserters disclosed herein are adapted to engage dynamic implants having an elongated bridge, or body, with connection means extending from each end of the bridge along the longitudinal direction established by the bridge. Each dynamic implant has a free state, or a relaxed state, when no external forces act upon the implant (other than gravity), and an elastically deformed state, when the bridge is flexed against the resistance of the inserter supporting the connection means. An example implant 400 is shown in FIGS. 15-22.

Referring to FIGS. 1-6, an implant inserter 100 may include a body 102, a carriage 104, a lever 106, a screw 108, a lever pin 110, and a carriage pin 112.

The body 102 extends between a distal end 150 and a proximal end 152. The body 102 is an elongated plate-like part. The distal end 150 includes an undercut rail 154 that extends across the distal aspect of the body 102 along a top-bottom direction. The rail 154 may be referred to as a ram or a ram head. The rail 154 may overhang, or extend past, the bottom side of the body 102. The bottom-most aspect 166 of the rail 154 may be convex in a front view. The rail 154 is shown as a T-rail, but other undercut geometries are contemplated, such as a dovetail rail. The distal end 150 includes bilateral bosses 156, 158 which extend from the top side of the body 102 proximal to the rail 154. The bosses 156, 158 are separated by a gap 160. A transverse hole 162 extends through both bosses 156, 158 along a left-right direction. An internally threaded hole 164 extends through the body 102 proximal to the bosses 156, 158 along a top-bottom direction.

Figure 5:
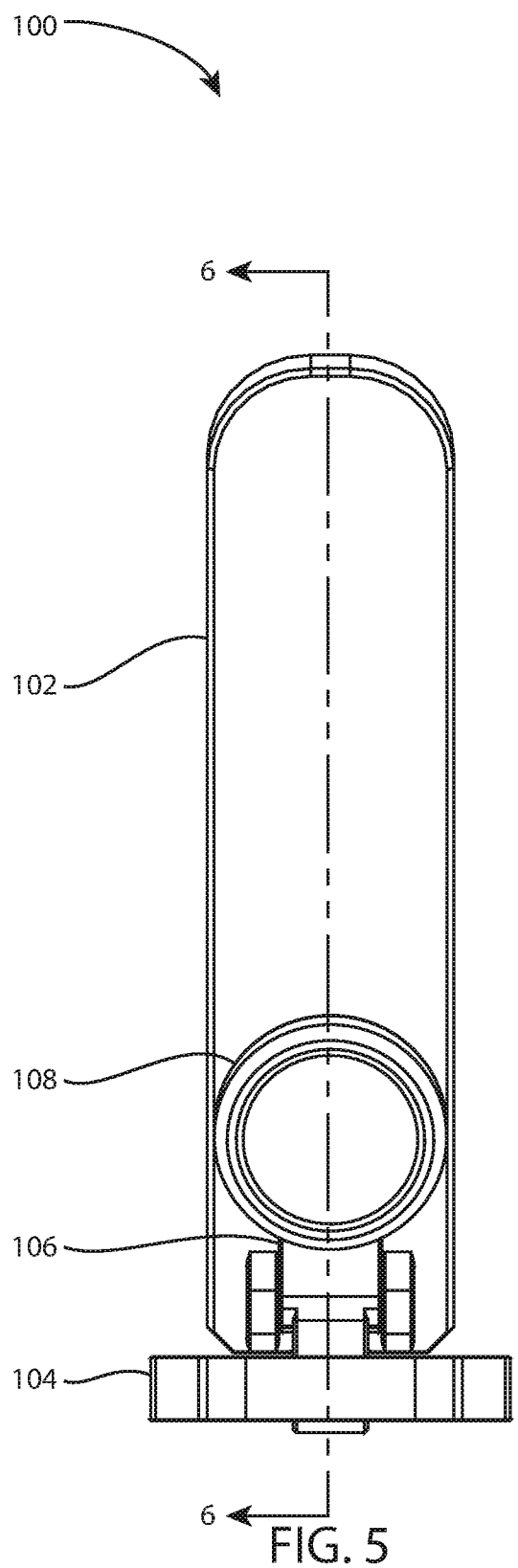
FIG. 5 is a top view of the implant inserter of FIG. 1.

The carriage 104 extends between a bottom end 118 and a top end 120. The carriage 104 may have a rectangular overall shape in a top or bottom view (FIG. 5). In a front or back view, the top portion of the carriage 104 may be rectangular, while the bottom portion may flare outwardly toward the bottom end 118. The bottom-most aspect of the carriage 104 may include two jaws or hooks 122, 124 that face each other across a shallow alcove 126 with a top surface 142 that faces down (bottom). The hooks 122, 124 include top surfaces 128, 130, respectively. The hooks 122, 124 include back walls 132, 134, respectively. Thus the hooks 122, 124 are suitable for front loading an implant. However, one wall 132, 134 may optionally be a front wall, similar to the arrangement of walls 222, 224 discussed below, or both walls 132, 134 may be front walls, similar to walls 332, 334 discussed below. An undercut channel 136 extends from a central portion of the alcove 126 across the back side of the carriage toward the top end 120. The undercut channel 136 may terminate before reaching the top end 120. The undercut channel 136 is shown as a T-slot, but other undercut geometries are contemplated, such as a dovetail slot. A window 138 extends through the carriage 104 between the front and back sides. The window 138 may be centered in the left-right width of the carriage and may intersect the top portion of the undercut channel 136. A transverse hole 140 extends left-right through the carriage and intersects the undercut channel 136 near the middle of the window 138.

Figure 6:
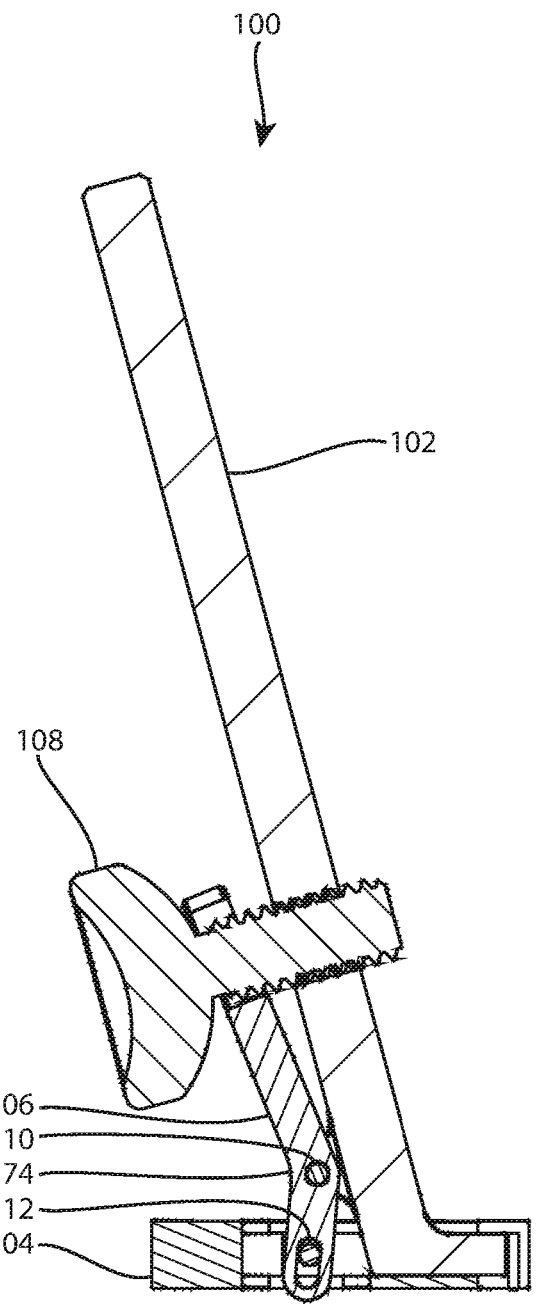
FIG. 6 is a cross-sectional view of the implant inserter of FIG. 1, taken along section line 6-6 of FIG. 5.
Figure 7:
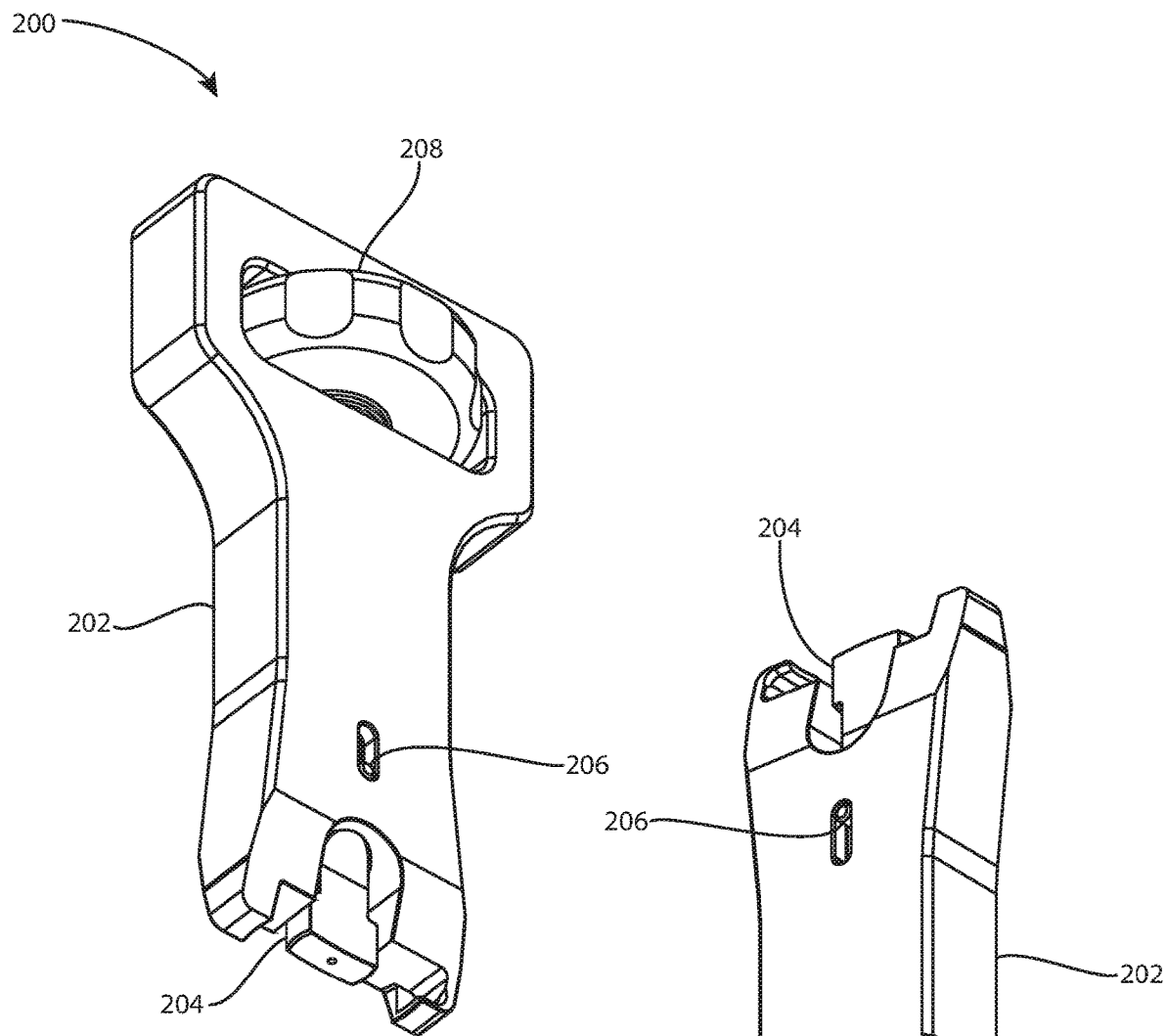
FIG. 7 is a perspective view of another implant inserter.
Figure 8:
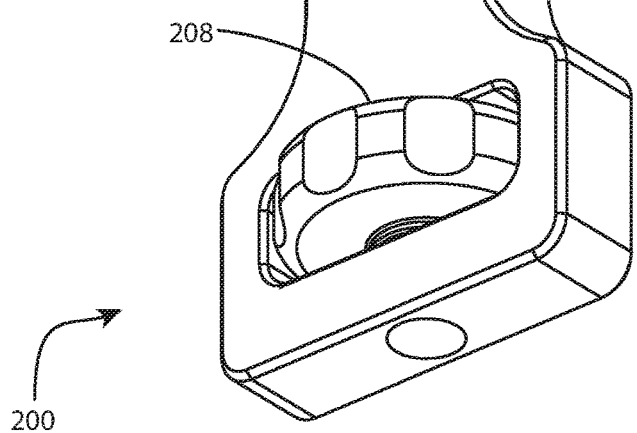
FIG. 8 is another perspective view of the implant inserter of FIG. 7 from a different direction.
Figure 9:
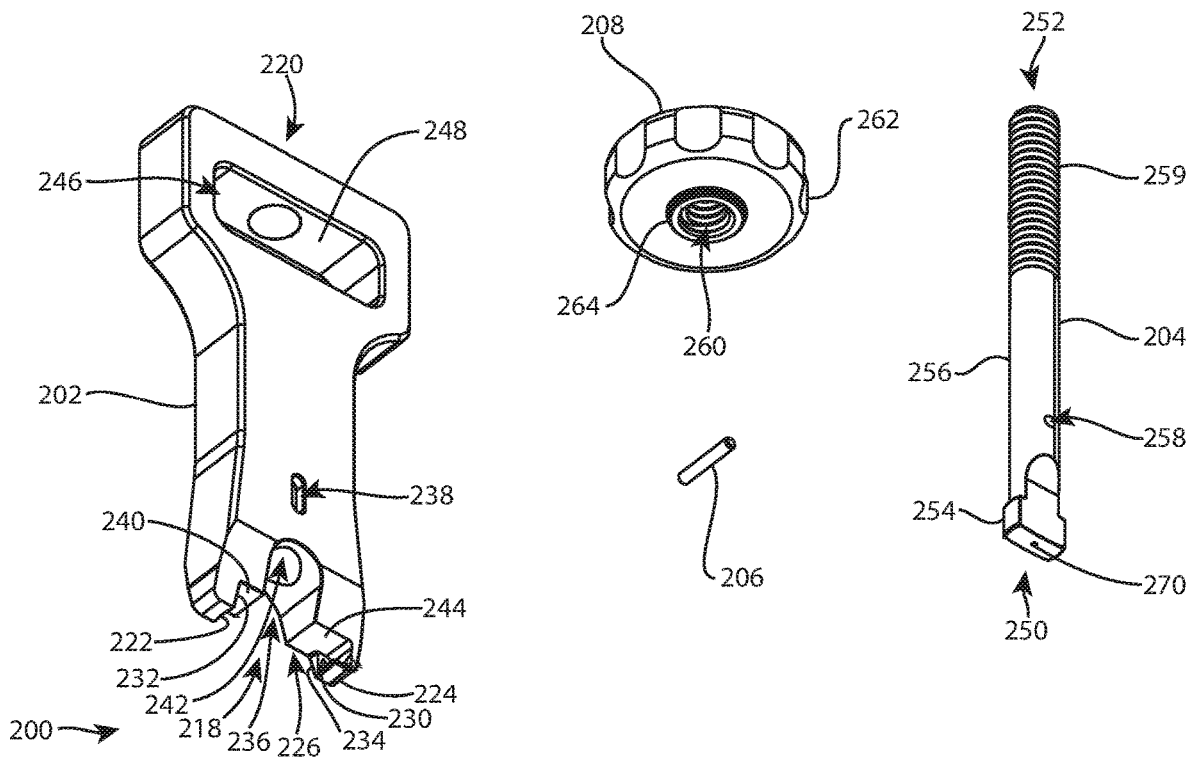
FIG. 9 is an exploded perspective view of the implant inserter of FIG. 7.
Figure 10:
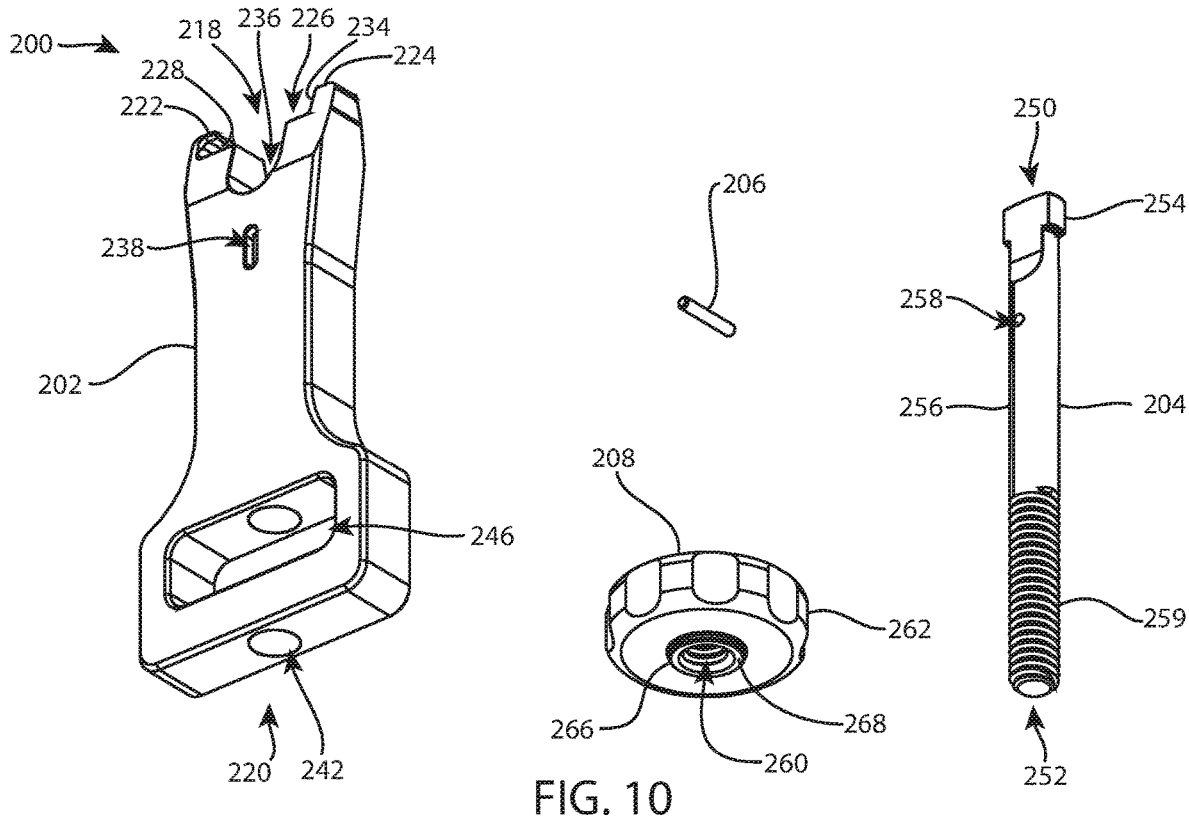
FIG. 10 is another exploded perspective view of the implant inserter of FIG. 7 from a different direction.
Figure 11:
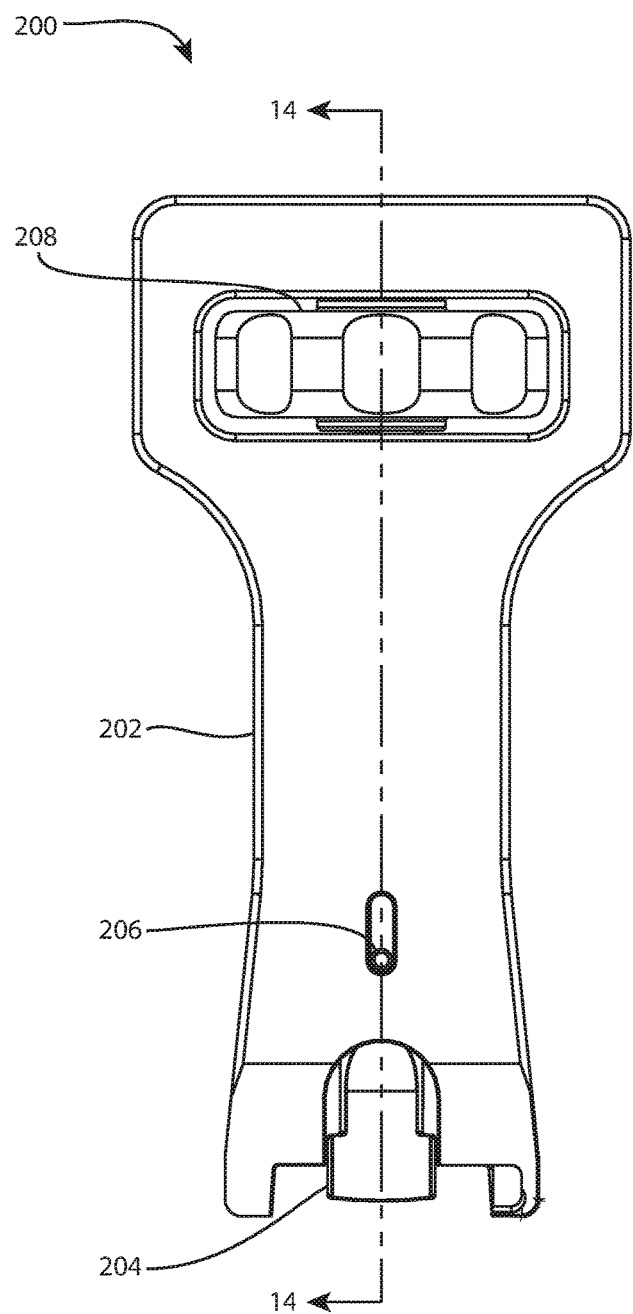
FIG. 11 is a front view of the implant inserter of FIG. 7.
Figure 12:
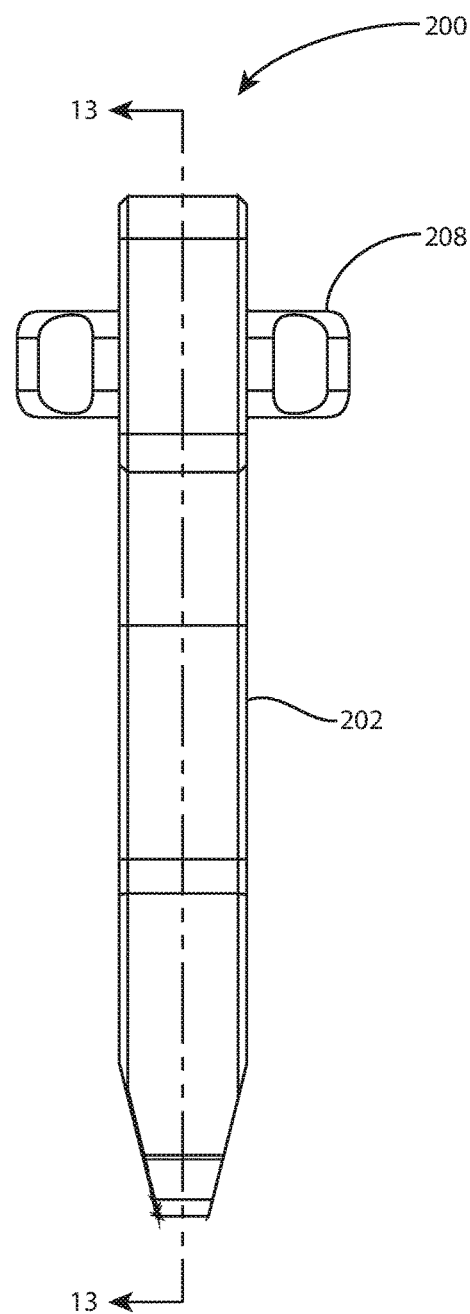
FIG. 12 is a right view of the implant inserter of FIG. 7.
Figure 13:
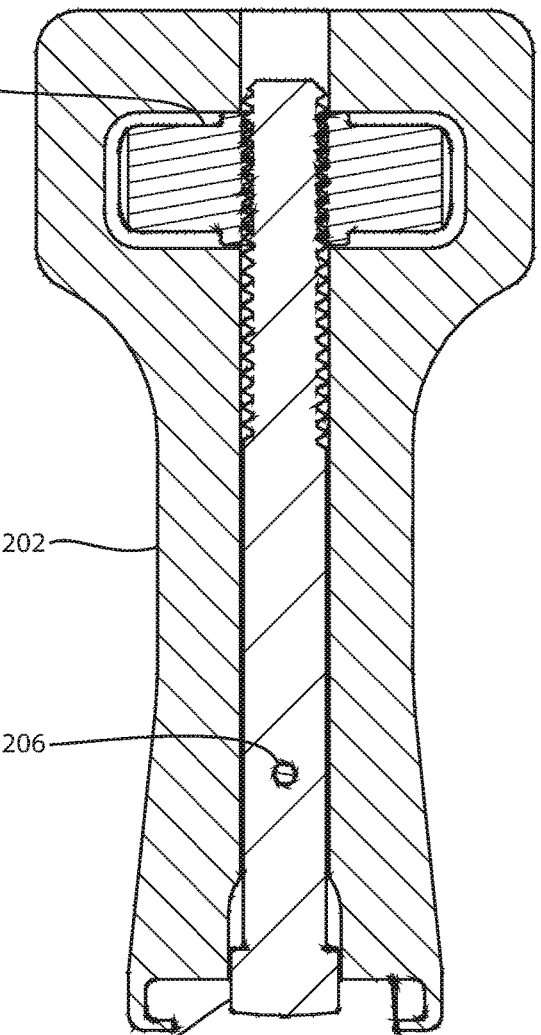
FIG. 13 is a cross-sectional view of the implant inserter of FIG. 7, taken along section line 13-13 of FIG. 12.
Figure 14:
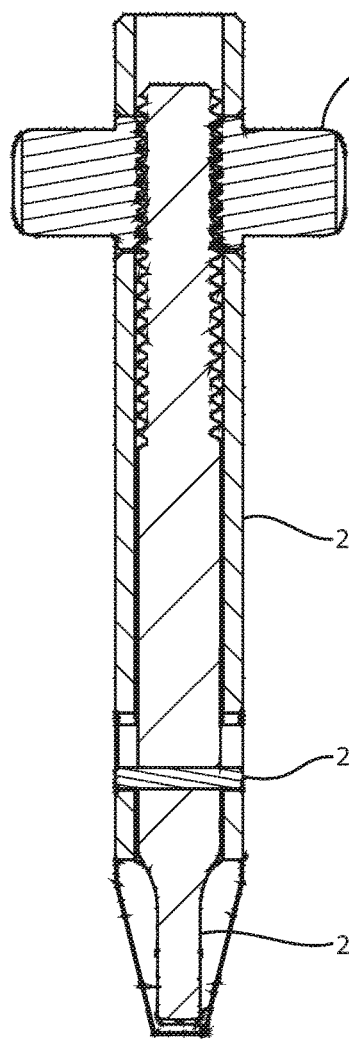
FIG. 14 is a cross-sectional view of the implant inserter of FIG. 7, taken along section line 14-14 of FIG. 11.

The lever 106 extends between a distal end 170 and a proximal end 172. The lever 106 may be an elongated plate-like part with a bend 174 seen best in a left or right side view (FIG. 6). An elongated slot 176 may extend through the lever 106 along a left-right direction near the distal end 170. The slot 176 may be oval as shown, or another elongated shape. A transverse hole 178 may extend through the lever 106 along the left-right direction near the bend 174. Distally-facing shoulders 180, 182 may be formed around each end of the hole 178. A slot or notch 184 may extend distally into the proximal end 172, dividing the proximal end 172 into prongs 186, 188.

The screw 108 includes a head 190 and an externally threaded shaft 192 extending from the head.

The inserter 100 may be operatively assembled by inserting the lever 106 into the gap 160 between the bosses 156, 158 of the body 102 so that the convex side of the bend 174 faces the body 102 and the distal ends 150, 170 face the same direction; inserting the lever pin 110 through the holes 162, 178 of the body 102 and lever 106; passing the externally threaded shaft 192 of the screw 108 between the prongs 186, 188 of the lever 106 and threading the shaft 192 into the hole 164 of the body 102; inserting the distal end 170 of the lever 106 into the window 138 of the carriage 104; sliding the rail 154 of the body 102 into the bottom end of the channel 136 of the carriage 104; and inserting the carriage pin 112 through the hole 140 of the carriage 104 and the slot 176 of the lever 106.

When the inserter 100 is operatively assembled, the carriage 104, lever 106, screw 108, lever pin 110, and carriage pin 112 are captive to the body 102, although the screw 108 is readily removable. Turning the screw 108 clockwise and counterclockwise moves the proximal end 172 of the lever 106 closer to, or farther from, the body 102. The lever 106 may be biased toward the head 190 of the screw 108 or toward the body 102, for example with a spring element. Preferably, the lever 106 is biased toward the head 190 of the screw 108. The distal end 170 of the lever 106 moves in the opposite direction as the proximal end 172 due to the hinge formed by the lever pin 110 in the holes 162, 178. The carriage 104 moves with the distal end 170 of the lever 106 due to the pinned connection of the carriage pin 112 in the hole 140 and slot 176. Thus, turning the screw 108 causes the carriage 104 to move relative to the body 102. More specifically, turning the screw 108 causes the hooks 122, 124 to move along a bottom-top direction relative to the rail 154. However, there is no relative rotation between the carriage 104 and the body 102.

With brief reference to the clip 400 shown in FIGS. 15-22 and discussed in detail below, the clip 400 and inserter 100 may be operatively assembled by turning the screw 108 to lower the hooks 122, 124 relative to the rail 154 so that the bottom aspect 166 of the rail 154 is within the channel 136 of the carriage 104; sliding the hooks 122, 124 into engagement with the connecting means 414, 416; and turning the screw 108 to raise the hooks 122, 124 relative to the rail 154 so that the bottom aspect 166 of the rail 154 contacts the bridge 406. The connecting means 414, 416 may contact the back walls 132, 134.

When the clip 400 and inserter 100 are operatively assembled, clockwise and counterclockwise rotation of the screw 108 causes the bridge 406 to move between an elastically deformed state and a relaxed state, or free state. In the elastically deformed state, the bottom aspect 166 of the rail 154 presses against the proximal surface 408 of the bridge 406, flattening the bridge against the resistance of the connecting means 414, 416 in the hooks 122, 124 and spreading apart the free ends 436, 440 of the bone engaging members 402, 404. In the relaxed state, the bottom aspect 166 of the rail 154 may be spaced apart from the proximal surface 408 of the bridge 406, or may contact the proximal surface 408 so lightly that the bridge remains undeformed.

Referring to FIGS. 7-14, another implant inserter 200 may include a body 202, a ram 204, a ram pin 206, and a knob 208.

The body 202 extends between a distal end 218 and a proximal end 220. The body 202 may be a generally plate-like part that is wider at the distal end 218 and narrower at the proximal end 220. The distal-most aspect of the body 202 may include two jaws or hooks 222, 224 that face each other across a shallow alcove 226 with a proximal surface 240 that faces distally. Two proximal surfaces 240, 244 are shown; they may be coplanar. The hooks 222, 224 include proximal surfaces 228, 230, respectively. The hook 222 includes a front wall 232 and the hook 224 includes a back wall 234. Thus the hooks 222, 224 are suitable for pivotably loading an implant. However, both walls 232, 234 may optionally be on the same side, front or back, similar to the walls 122, 124 discussed above or the walls 322, 324 discussed below. A notch 236 extends proximally from a central portion of the alcove 226. A central longitudinal slot 238 or window extends between the front and back sides of the body 202 proximal to the notch 236. A central longitudinal hole 242 extends proximally through the body 202 between the distal and proximal ends 218, 220. A transverse window 246 extends between the front and back sides of the body 202 near the proximal end 220, and may intersect the hole 242. The window 246 may have a proximal surface 248 which faces distally.

The ram or shaft 204 extends between a distal end 250 and a proximal end 252. The ram 204 includes a distal head 254, which may be generally rectangular as shown. As seen best in FIGS. 11 and 13, the distal-most aspect 270 of the head 254 may be convex in a front or back view. A shaft 256 extends proximally from the head 254. The shaft 256 may have a circular cross section as shown. The outer diameter of the shaft 256 may be greater than the thickness of the head 254 in a front-back direction, and may be less than the width of the head in a left-right direction, as seen best in FIGS. 13 and 14. A transverse hole 258 extends through the shaft 256 proximal to the head 254. The proximal end 252 of the ram 204 may include external threads 259.

The knob 208 may include a generally cylindrical body 262. A central longitudinal internally threaded hole 260 may extend through the knob 208 along a proximal-distal direction. The knob 208 may include a first boss 264 extending distally from the body 262 concentric with the hole 260, and a second boss 266 extending proximally from the body concentric with the hole. The second boss 266 may have a proximal surface 268 which faces proximally.

The inserter 200 may be operatively assembled by inserting the knob 208 in the window 246 of the body 202, inserting the proximal end 252 of the ram 204 into the distal end 218 of the hole 242, threading the proximal external threads 259 into the internally threaded hole 260 to draw the ram 204 proximally so that the hole 258 is exposed in the slot 238, and inserting the pin 206 through the slot 238 and hole 258.

When the inserter 200 is operatively assembled, the ram 204, pin 206, and knob 208 are captive to the body 202. Clockwise and counterclockwise rotation of the knob 208 causes the ram 204 to translate along the proximal-distal direction. The pin 206 in the slot 238 prevents the ram 204 from rotating and limits the proximal and distal travel of the ram.

The clip 400 and inserter 200 may be operatively assembled by turning the knob 208 to move the ram 204 proximally so that the distal aspect 270 of the head 254 is within the notch 236; sliding the hooks 222, 224 over the connecting means 414, 416; and turning the knob 208 to move the ram 204 distally so that the distal aspect 270 of the head 254 contacts the bridge 406. Sliding the hooks 222, 224 into engagement with the connecting means 414, 416 may involve pivoting or rotating the hooks relative to the connecting means, or vice versa. The connecting means 414, 416 may contact the front and back walls 232, 234.

When the clip 400 and inserter 200 are operatively assembled, clockwise and counterclockwise rotation of the knob 208 causes the bridge 406 to move between an elastically deformed state and a relaxed state, or free state. In the elastically deformed state, the distal aspect 270 of the head 254 presses against the proximal surface 408 of the bridge 406, flattening the bridge against the resistance of the connecting means 414, 416 in the hooks 222, 224 and spreading apart the free ends 436, 440 of the bone engaging members 402, 404. The force of the head 254 against the bridge 406 may also be resisted by the proximal surface 268 of the second boss 266 of the knob 208 against the proximal surface 248 of the window 246 of the body 202. In the relaxed state, the distal aspect 270 of the head 254 may be spaced apart from the proximal surface 408 of the bridge 406, or may contact the proximal surface 408 so lightly that the bridge remains undeformed.

Referring to FIGS. 15-22, a clip 400 and yet another inserter 300 are shown operatively assembled, with the clip 400 in the free state, or relaxed state.

The clip 400 is shown with an optional integrated anti-torque plug 450. Clip 400 may also be referred to as a fastener, staple, or implant. The clip 400 may be a compression bone staple. Anti-torque plug 450 may also be referred to as a tab, keel, post, or implant. One or more clips 400 may be implanted in a single procedure, for example to join two bone portions together.

Figure 17:
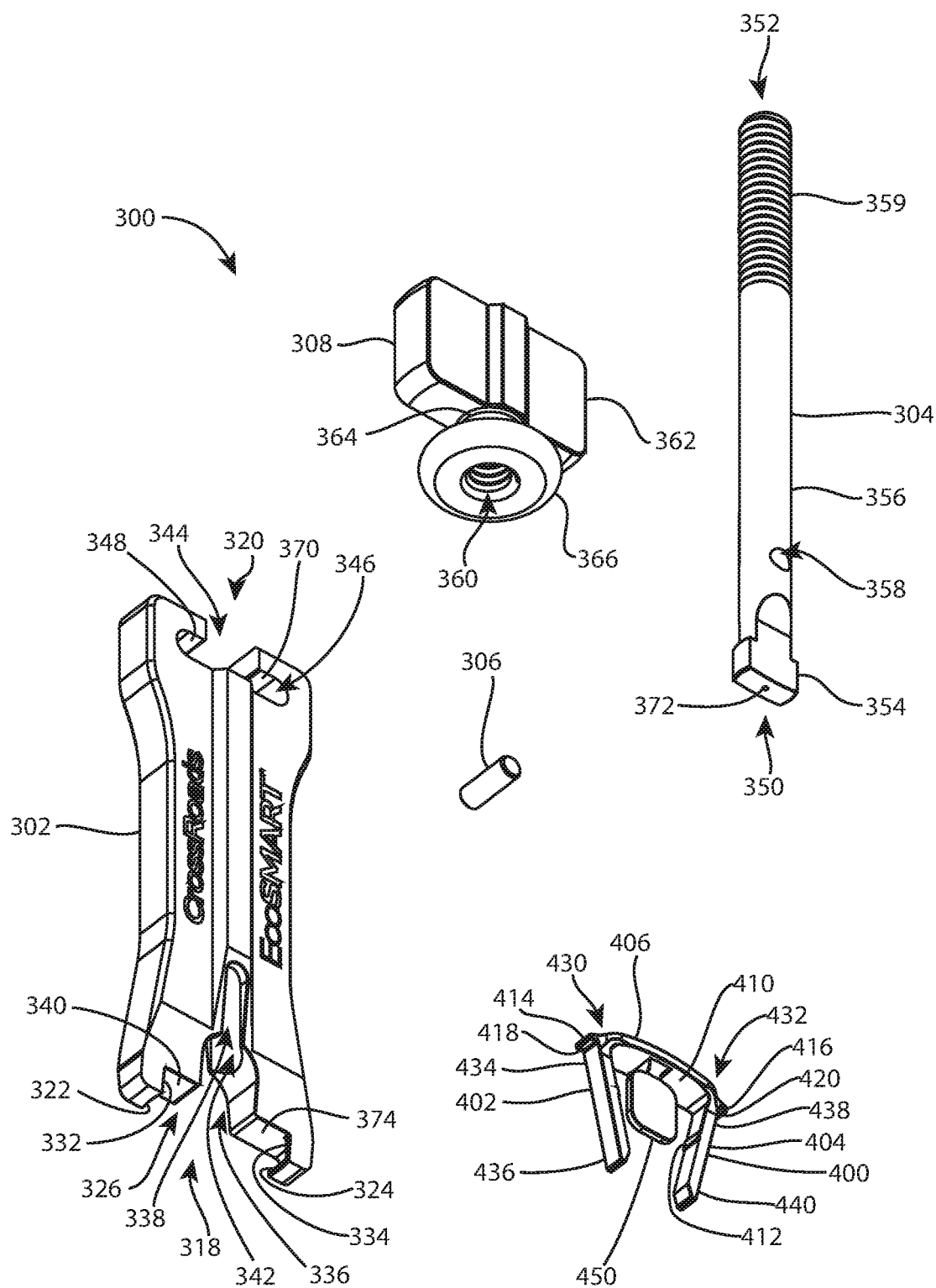
FIG. 17 is a perspective exploded view of the implant and implant inserter of FIG. 15.
Figure 18:
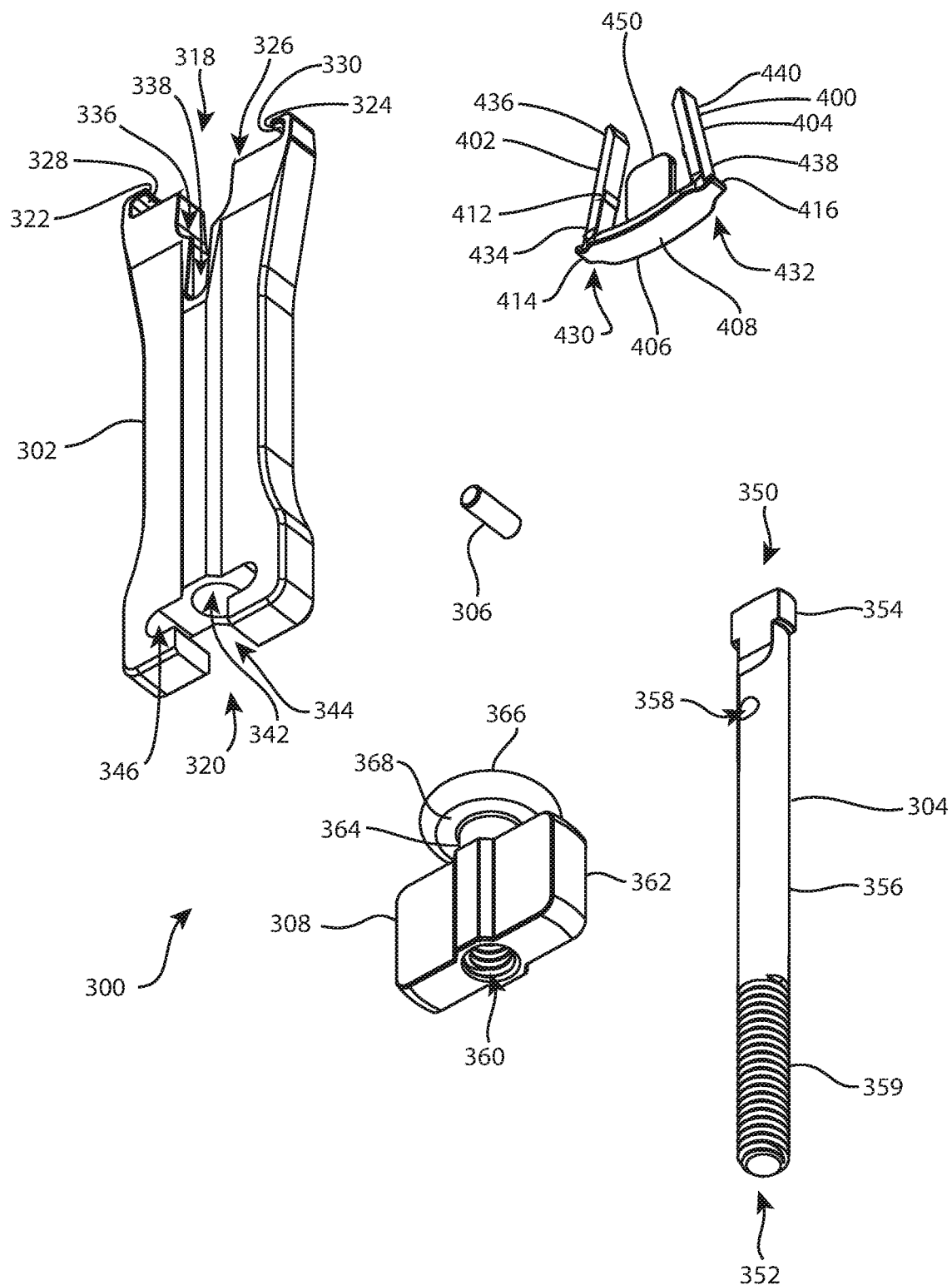
FIG. 18 is another perspective exploded view of the implant and implant inserter of FIG. 15 from a different direction.

Referring to FIGS. 17 and 18, the clip 400 includes bone engaging members 402 and 404 which may be integral to a clip bridge 406, also referred to as a clip body. The bone engaging members 402 and 404 may be referred to as legs. In other embodiments within the scope of the disclosure, a clip may include more than two bone engaging members; or alternatively may include openings for one or more independent fasteners in lieu of the bone engaging members. In other embodiments of the disclosure, the implant 400 may be more similar to a plate. The bone engaging member 402 extends from a left end 430 of the clip bridge 406 and the bone engaging member 404 extends from an opposite right end 432 of the clip bridge 406. Bone engaging member 402 has a proximal end 434 attached to the left end 430 of the clip bridge 406 and an opposite distal end 436 which is a free end. Bone engaging member 404 has a proximal end 438 attached to the right end 432 of the clip bridge 406 and an opposite distal end 440 which is a free end. Clip bridge 406 has at least one upper or proximal surface 408 and at least one lower or distal surface 410. The lower surface 410 may be referred to as a bone facing surface. Bone engaging member 402 extends from the lower surface 410 beside bone engaging member 404. Referring to FIG. 18, the bridge 406 may decrease in thickness toward the left and right ends 430, 432 and connecting means 414, 416. The major front-back dimension of the bridge 406 may be 5 mm and the front-back dimension of the connecting means 414, 416 may be 2.7 mm. The bone engaging members 402 and 404 may have features 412 that may improve bone purchase or improve pull out strength of the clip 400 from bone or soft tissue. The features 412 may be referred to as teeth or serrations. The features 412 may be on facing sides of the bone engaging members 402, 404 or on any or all sides of the bone engaging members. The clip 400 may have projections or other connecting means 414 and 416 for connection with a means of insertion. The connecting means 414, 416 may be referred to as tabs, ears, protrusions, wings, retainers, or retaining members. The connecting means 414 and 416 are shown extending sideways outwardly from the left and right ends 430, 432 of the bridge 406, respectively, along a longitudinal direction established by the bridge. In other embodiments, the connecting means may project perpendicularly with respect to the bridge. The connecting means 414 and 416 may have lower or distal surfaces 418 and 420 respectively that may releasably engage with a means of insertion that may allow an inserter or other means of insertion to be side loading, top loading or pivotably loaded. For example, an inserter for clip 400 may be side loading or pivotably loading. The lower surfaces 418, 420 may be referred to as bone facing surfaces. Referring to FIG. 21, the lower surfaces 418, 420 are proximally spaced apart from, or proximally offset from, from the lower surface 410. The dashed extension lines 410' and 410" in FIG. 21 show the level of the lower surface 410 versus the lower surfaces 418, 420.

A means of insertion may maintain the clip 400 in a first configuration thereby allowing a second configuration once an inserter is disassembled from the implant. The first configuration may be an elastically deformed state, for example an insertion state. The second configuration may be a free state or an implanted state, as seen in FIG. 19. The means of insertion may utilize features similar to connecting means 414 and 416 in combination with other surfaces such as top surface 408. This combination of means of insertion may be used to maintain one or more features or arms or projections in a particular configuration. This combination of means of insertion may create a bending modality, such as a three point or four point bend, to maintain a specific clip device configuration or combination of configurations. A combination of surfaces and means of insertion, such as connecting means 414, may be used on the entire clip or portions of a clip to create or maintain a particular configuration of a clip. For example, a tab such as 414 and top surface, such as 408 may be used to maintain one side of a clip or one leg of a clip in a particular configuration. When disassembled, that leg may have a configuration that is different from or the same as the configuration of the rest of the clip.

Referring to FIG. 19, the clip 400 is shown in the free state, or relaxed state, which is the shape of the clip 400 when no external forces are acting upon the clip 400, other than gravity; the clip 400 experiences no elastic or plastic deflection or deformation. In the free state, the bone engaging members 402 and 404 converge as they extend away from the bridge 406 so that the distal ends 436, 440 are closer together than are the proximal ends 434, 438. An angle 422 is formed between the converging bone engaging members 402 and 404 in the free state. The angle 422 opens toward the bridge 406. The angle 422 may be referred to as a free state angle.

The inserter 300 may be used with the clip 400 and other implants. The inserter 300 may include a body 302, a ram or shaft 304, a pin 306, and a knob 308. The ram 304 and the ram pin 306 may be coupled together as a ram sub-assembly 314.

The body 302 extends between a distal end 318 and a proximal end 320. The body 302 may be a generally plate-like part that is wider at the distal and proximal ends 318, 320 and narrower in between. The distal-most aspect of the body 302 may include two jaws or hooks 322, 324 that face each other across a shallow alcove 326 with a proximal surface 340 that faces distally. Two proximal surfaces 340, 374 are shown; they may be coplanar. The hooks 322, 324 include proximal surfaces 328, 330, respectively. The hooks 322, 324 include front walls 332, 334, respectively. Thus the hooks 322, 324 are suitable for back loading an implant. However, one wall 332, 334 may optionally be a back wall, similar to the arrangement of walls 222, 224 discussed above, or both walls 332, 334 may be back walls, similar to walls 132, 134 discussed above. A first notch 336 extends proximally from a central portion of the alcove 326. A second notch 338 extends proximally from a central portion of the first notch 336. The second notch 338 is narrower than the first notch 336. A central longitudinal hole 342 extends proximally through the body 302 between the distal and proximal ends 318, 320. The body 302 may be thickened in the vicinity of the hole 342 so as to adequately support the hole 342 under expected loads. A third notch 344 extends distally into a central portion of the proximal end 320 and intersects a transverse slot 346 that extends between the front and back sides of the body 302. The transverse slot 346 may have a proximal surface 348 that faces distally. A second proximal surface 370 is also shown, which also faces distally and may be coplanar with the proximal surface 348.

The ram or shaft 304 extends between a distal end 350 and a proximal end 352. The ram 304 may be similar to, or identical to, the ram 204. The ram 304 includes a distal head 354, which may be generally rectangular as shown. As seen best in FIGS. 19 and 21, the distal-most aspect 372 of the head 354 may be convex in a front or back view. A shaft 356 extends proximally from the head 354. The shaft 356 may have a circular cross section as shown. The outer diameter of the shaft 356 may be greater than the thickness of the head 354 in a front-back direction, and may be less than the width of the head in a left-right direction, as seen best in FIGS. 21 and 22. A transverse hole 358 extends through the shaft 356 proximal to the head 354. The proximal end 352 of the ram 304 may include external threads 359.

The ram 304 and the ram pin 306 may be coupled together to form the ram sub-assembly 314 by inserting the ram pin through the hole 358. The ram pin 306 may be fixed within the hole 358 by a press fit, swaging operation, welding or brazing operation, or the like.

The knob 308 may include a generally rectangular body 362 which may be contoured to match the proximal end 320 of the body 302. A central longitudinal internally threaded hole 360 may extend through the knob 308 along a proximal-distal direction. The knob 308 may include a first shaft portion 364 extending distally from the body 362 concentric with the hole 360. The outer diameter of the first shaft portion 364 may be less than the outer dimensions of the body 362 in a front, back, left, or right view. A second shaft portion 366 may extend distally from the first shaft portion 364 concentric with the hole 360. The outer diameter of the second shaft portion 366 may be greater than the outer diameter of the first shaft portion 364 so that the second shaft portion has a proximal surface 368 that faces proximally.

The inserter 300 may be assembled by coupling the knob 308 to the body 302 so that the first shaft portion 364 is in the third notch 344 and the second shaft portion 366 is in the transverse slot 346; inserting the ram pin 306 into the hole 358 of the ram 304 to form the ram sub-assembly 314; inserting the proximal end 352 of the ram into the distal end of the hole 342 of the body 302; advancing the ram proximally until the proximal end 352 reaches the knob 308; and engaging the external and internal threads 359, 360 so that the head 354 is received in the first notch 336 and the pin 306 is received in the second notch 338.

When the inserter 300 is assembled, the ram 304, pin 306, and knob 308 are captive to the body 302. Clockwise and counterclockwise rotation of the knob 308 causes the ram 304 to translate along the proximal-distal direction. The pin 306 in the second notch 338 prevents the ram 304 from rotating and limits the proximal travel of the ram. However, there is no limit to the distal travel of the ram in this embodiment, so that the inserter 300 is readily disassembled for cleaning.

The clip 400 and inserter 300 may be operatively assembled by turning the knob 308 to move the ram 304 proximally so that the distal aspect 372 of the head 354 is within the first notch 336; sliding the hooks 322, 324 over the connecting means 414, 416; and turning the knob 308 to move the ram 304 distally so that the distal aspect 372 of the head 354 contacts the bridge 406. The connecting means 414, 416 may contact the front walls 332, 334.

When the clip 400 and inserter 300 are operatively assembled, clockwise and counterclockwise rotation of the knob 308 causes the bridge 406 to move between an elastically deformed state and a relaxed state, or free state. In the elastically deformed state, the distal aspect 372 of the head 354 presses against the proximal surface 408 of the bridge 406, flattening the bridge against the resistance of the connecting means 414, 416 in the hooks 322, 324 and spreading apart the free ends 436, 440 of the bone engaging members 402, 404. The force of the head 354 against the bridge 406 may also be resisted by the proximal surface 368 of the second shaft portion 366 of the knob 308 against the proximal surface(s) 348 and/or 370 of the transverse slot 346 of the body 302. In the relaxed state, the distal aspect 372 of the head 354 may be spaced apart from the proximal surface 408 of the bridge 406, or may contact the proximal surface 408 so lightly that the bridge remains undeformed.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. An inserter for a dynamic implant having an elongated bridge and first and second connecting means extending from first and second ends of the bridge, wherein the bridge has a proximal surface, wherein the bridge and the first and second connecting means each have a distal surface, the inserter comprising:

a body;

a knob, wherein the knob is captive to the body within a slot in a proximal portion of the body;

first and second hooks, wherein the first and second hooks face each other across an alcove, wherein the first and second hooks each have a proximal surface, wherein the alcove has a proximal surface that is proximal to the proximal surfaces of the first and second hooks; and a ram comprising a ram head and a ram shaft, wherein the ram head has a distal surface, wherein the ram head is movable relative to the first and second hooks between a proximal position and a distal position, wherein in the proximal position, the distal surface of the ram head is proximal to the proximal surface of the alcove, wherein in the distal position, the distal surface of the ram head is distal to the proximal surface of the alcove, wherein the ram shaft extends proximally from, and is integrally formed with, the ram head, wherein a proximal portion of the ram shaft is threaded;

wherein a distal portion of the body comprises the first and second hooks, wherein the ram shaft is received in the body, wherein the knob comprises a threaded hole, wherein the proximal portion of the ram shaft threads into the knob hole;

wherein when the inserter is connected to the implant, the first and second hooks receive the first and second connecting means, the proximal surfaces of the first and second hooks contact the distal surfaces of the first and second connecting means, the alcove receives the bridge, and the distal surface of the ram head faces the proximal surface of the bridge;

wherein when the inserter is connected to the implant and the ram head is in the proximal position, the implant is in a relaxed state in which the bridge is undeformed;

wherein when the inserter is connected to the implant and the ram head is in the distal position, the implant is in an elastically deformed state in which the bridge is elastically deformed.

2. The inserter of claim 1, wherein when the ram head moves between the proximal and distal positions, the ram head does not rotate relative to the first and second hooks.

3. The inserter of claim 1, wherein when the inserter is connected to the implant, the distal surface of the ram head contacts the proximal surface of the bridge.

4. A system for implant elastic deformation and insertion, comprising:
- an implant movable between a relaxed state and an elastically deformed state, wherein the implant comprises an elongated bridge and first and second connecting means, wherein the bridge extends between opposite first and second ends and has a distal surface and an opposite proximal surface, wherein the first connecting means extends from the first end of the bridge, wherein the second connecting means extends from the second end of the bridge, wherein each of the first and second connecting means has a distal surface, wherein when the implant is in the relaxed state, the bridge is undeformed; wherein when the implant is in the elastically deformed state, the bridge is elastically deformed; and
- an inserter comprising a body, a knob captive to the body within a slot in a proximal portion of the body, a ram for engaging the bridge, and first and second hooks for engaging the connecting means, wherein a distal portion of the body comprises the first and second hooks, wherein the knob comprises a threaded hole, wherein the ram has a distal surface integrally formed with a proximal threaded ram shaft, wherein the ram shaft is received in the body and threads into the knob hole, wherein each of the first and second hooks has a proximal surface, wherein the first and second hooks are movable together relative to the ram between a distal position and a proximal position, wherein in the distal position, the proximal surfaces of the first and second hooks are distal to the distal surface of the ram by a first distance, wherein in the proximal position, the proximal surfaces of the first and second hooks are distal to the distal surface of the ram by a second distance, wherein the second distance is less than the first distance;
- wherein when the inserter is connected to the implant, the first and second hooks receive the first and second connecting means, the proximal surfaces of the first and second hooks contact the distal surfaces of the first and second connecting means, and the distal surface of the ram faces the proximal surface of the bridge;
- wherein when the inserter is connected to the implant and the first and second hooks are in the distal position, the implant is in the relaxed state;
- wherein when the inserter is connected to the implant and the first and second hooks are in the proximal position, the implant is in the elastically deformed state.

5. The system of claim 4, wherein the ram does not rotate relative to the first and second hooks.

6. The system of claim 4, wherein when the inserter is connected to the implant, the distal surface of the ram contacts the proximal surface of the bridge.

* * * * *